US006632631B1

(12) United States Patent
Shuster et al.

(10) Patent No.: US 6,632,631 B1
(45) Date of Patent: Oct. 14, 2003

(54) METHODS FOR THE IDENTIFICATION OF INHIBITORS OF HOMOCITRATE SYNTHASE AS ANTIBIOTICS

(75) Inventors: Jeffrey Shuster, Chapel Hill, NC (US); Matthew M. Tanzer, Durham, NC (US); Lisbeth Hamer, Durham, NC (US); Kiichi Adachi, Durham, NC (US); Todd M. DeZwaan, Apex, NC (US); Sze-Chung Lo, Durham, NC (US); Maria Victoria Montenegro-Chamorro, Morrisville, NC (US); Blaise Darveaux, Hillsborough, NC (US); Sheryl Frank, Durham, NC (US); Ryan Heiniger, Raleigh, NC (US); Sanjoy K. Mahanty, Chapel Hill, NC (US); Huaqin Pan, Apex, NC (US); Amy Skalchunes, Raleigh, NC (US); Rex W. Tarpey, Apex, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 75 days.

(21) Appl. No.: 10/011,200

(22) Filed: Nov. 9, 2001

(51) Int. Cl.[7] .......................... C12Q 1/18; C12Q 1/26; C12Q 1/37

(52) U.S. Cl. .......................... 435/32; 435/25; 435/24; 435/23; 424/195.15; 424/195.16

(58) Field of Search .......................... 435/32, 25, 24, 435/23; 424/195.15, 195.16

(56) References Cited

U.S. PATENT DOCUMENTS

| | | | |
|---|---|---|---|
| 4,920,109 A | 4/1990 | Onishi et al. | 514/171 |
| 4,920,111 A | 4/1990 | Onishi et al. | 514/171 |
| 4,920,112 A | 4/1990 | Onishi et al. | 514/171 |
| 4,920,113 A | 4/1990 | Onishi et al. | 514/171 |
| 4,921,844 A | 5/1990 | Onishi et al. | 514/171 |
| 5,976,848 A | 11/1999 | Davis et al. | 435/183 |
| 6,074,830 A | 6/2000 | Bacot et al. | 435/6 |

OTHER PUBLICATIONS

Gaillardin et al; Biochim. Biophys. Acta; V 422(2): p 390–406; (Feb. 13, 1976).*

Webster's Dictionary; p 113; 1984.*

Aufauvre–Brown, Agnes et al., "*Aspergillus fumigatus* chsE: A Gene Related to CHS3 of *Saccharomyces cerevisiae* and Important for Hyphal Growth and Conidiophore Development but Not Pathogenicity." Fungal Genetics and Biology (1997) 21: 141–152.

Tang, Christoph M. et al., "Virulence Studies of *Aspergillus nidulans* Mutants Requiring Lysine or p–Aminobenzoic Acid in Invasive Pulmonary Aspergillosis." Infection and Immunity (1994) Dec.: 5255–5260.

Brown, Jeremy S. et al., "Signature–tagged and directed mutagenesis identify PABA synthetase as essential for *Aspergillus fumigatus* pathocenicity." Molecular Microbiology (2000) 36(6): 1371–1380.

(List continued on next page.)

*Primary Examiner*—Louise N. Leary
(74) *Attorney, Agent, or Firm*—Deborah H. Spencer; Timothy G. Hofmeyer; Laura L. Kiefer

(57) ABSTRACT

The present inventors have discovered that homocitrate synthase is essential for fungal pathogenicity. Specifically, the inhibition of homocitrate synthase gene expression in fungi results in no signs of successful infection or lesions. Thus, homocitrate synthase can be used as a target for the identification of antibiotics, preferably antifungals. Accordingly, the present invention provides methods for the identification of compounds that inhibit homocitrate synthase expression or activity. The methods of the invention are useful for the identification of antibiotics, preferably antifungals.

45 Claims, 4 Drawing Sheets

The function of the homocitrate synthase enzyme is the interconversion of Acetyl CoA, 2-oxoglutarate, and $H_2O$ to 2-hydroxybutane-1,2,4-tricarboxylate and CoA. This reaction is part of the lysine biosynthesis pathway.

OTHER PUBLICATIONS

D'Enfert, Christophe., "Attenuated Virulence of Uridine–Uracil Auxtrophs of *Aspergillus fumigatus*." Infection and Immunity (1996) Oct.: 4401–4405.

Hensel, M. et al,"The role of the *Aspergillus fumigatus* areA gene in invasive pulmonary aspergillosis." Mol Gen enet (1998): 553–557.

Shibuya, Kazutoshi et al., "Histopathology of experimental invasive pulmonary aspergillosis in rats: Pathological comparison of pulmonary lesions induced by specific virulent factor deficient mutants." Microbial Pathogenesis (1999) 27: 123–131.

Smith, Joanne M. et al., "Virulence of *Aspergillus fumigatus* Double Mutants Lacking Restrictocin and an Alkaline Protease in a Low–Dose Model of Invasive Pulmonary Apergillosis." Infection and Immunity (1994) Dec.: 5247–5254.

Reichard U. et al, Virulence of an aspergillopepsin–deficient mutant of *Aspergillus fumigatus* and evidence for another aspartic proteinase linked to the fungal cell wall. J Med Vet Mycol (1997) May–Jun.; 35 (3): 189–96.

Jaklitsch, Walter. M. et al. "Homocitrate synthase from Penicillium chrysogenum. Localization, purification of the cytosolic isoenzyme, and sensitivity to lysine": Biochem. J.(1990); vol. 269:pp. 247–253.

Tucci, Anthony F. et al. Homocitrate Synthase from Yeast; Archives of Biochemistry and Biophysics:1972; vol. 153: pp. 742–750.

* cited by examiner

Acetyl CoA + $H_2O$ + 2-oxoglutarate 2-hydroxybutane-1,2,4-tricarboxylate + CoA

The function of the homocitrate synthase enzyme is the interconversion of Acetyl CoA, 2-oxoglutarate, and $H_2O$ to 2-hydroxybutane-1,2,4-tricarboxylate and CoA. This reaction is part of the lysine biosynthesis pathway.

SEQUENCE LISTING

```
<160> NUMBER OF SEQ ID NOS: 3

<210> SEQ ID NO 1
<211> LENGTH: 1458
<212> TYPE: DNA
<213> ORGANISM: Magnaporthe grisea

<400> SEQUENCE: 1

atgtgcccat cctgcgagcc tgagcaagcc gctgcctcca atggcaatgc gaacggcaat     60

ggcgcctcca atggcaatgg aaaccacgac ggaatgactg gtattgagac tcgccaagca    120

caaaacgcac gctaccagcc atcacggaat ccctaccagc ccgtcggtga ctttttgtcc    180

aacgtgaaca acttcaagat cattgagagc accctgcgag agggcgagca gttcgccaat    240

gccttcttcg acacggccaa gaagattgag atcgccaagg cgctggacga ctttggcgtc    300

gactacatcg agctcaccag cccggctgcc tcggagcagt ccaggcttga ctgcgctgcc    360

atctgcaagc tgggactcaa ggccaagatc ctcacccaca tcaggtgcca catggacgac    420

gcgcgcatcg ccgtcgagac cggtgttgac ggcgtcgaca ttgtcatcgg cacctcttcg    480

ttcctcatgg agcactcgca cggcaaggac atgacctaca tcaccaacac ggccattgag    540

gtcatcaact ttgtcaagag caagggcatc gaggtccgct tctcatccga ggactcgttc    600

cgcagcaacc tggttgacct gctgagcatc tactcgaccg tcgacaagat tggtgtcaac    660

cgtgtcggta ttgctgatac cgtcggttgc gcctcgcccc gccaggtcta cgacctggtc    720

aagaccctgc gtggtgttgt ctcttgtgac attgagacac acttccacaa cgacactggc    780
```

-continued

```
tgtgccatct caaatgcttt ttgcgctttg gaggccggtg ctacccacat cgacacgtgt    840

gtcctgggta tcggcgagcg taacggaatt acccctcttg gaggtctgat ggctcgcatg    900

attgtcggct ccaaggacta cgttctgagc aagtacaagc tgcacaagct caaggacatt    960

gaggagcttg ttgccgacgc cgttcaggtc aacattcctt tcaataacta catcactggt   1020

ttctgtgctt tcacccacaa ggccggtatc catgccaagg ctattctcaa gaacccctca   1080

acatatgaga ttattgaccc gactctgttc ggcatcactc gctatgtcca cttcgccagc   1140

agattgacgg gatggaacgc aatcaagagc agagcatcgc agctcaacat tgagatgacg   1200

gatgagcagt gcaaggagtg cactgccaag atcaagctgt tggctgacat taggccgatc   1260

gctatcgacg acgccgactc catcattcac gcattccacc gcagcatcaa ctcgggccag   1320

cctattcagt ctctcggaag cctgctcccc aacatgacgg aggaggagaa ggccgccctg   1380

gcagatgtag agcgccgtga gtcgaacgat gccgagcaac cggcggccaa gagggccaag   1440

gtcgaggctg ttgcatga                                                 1458


<210> SEQ ID NO 2
<211> LENGTH: 2346
<212> TYPE: DNA
<213> ORGANISM: Magnaporthe grisea
<220> FEATURE:
<221> NAME/KEY: exon
<222> LOCATION: (130)..(384)
<223> OTHER INFORMATION:
<220> FEATURE:
<221> NAME/KEY: exon
<222> LOCATION: (551)..(1041)
<223> OTHER INFORMATION:
<220> FEATURE:
<221> NAME/KEY: exon
<222> LOCATION: (1101)..(1349)
<223> OTHER INFORMATION:
<220> FEATURE:
<221> NAME/KEY: exon
<222> LOCATION: (1415)..(1459)
<223> OTHER INFORMATION:
<220> FEATURE:
<221> NAME/KEY: exon
<222> LOCATION: (1518)..(1572)
<223> OTHER INFORMATION:
<220> FEATURE:
<221> NAME/KEY: exon
<222> LOCATION: (1649)..(2009)
<223> OTHER INFORMATION:
<220> FEATURE:
<221> NAME/KEY: misc_feature
<223> OTHER INFORMATION: Connect exons 1 to 6 for coding sequence (CDS)

<400> SEQUENCE: 2

caaagctgga gctccaccgc ggtggcggcc gctctagaac tagtggatcc cccgggctgc     60

aggaattcgg cacgagccaa gtcccagcct cccattgagc tttactcaca acaatcccaa    120

accaccaaa atg tgc cca tcc tgc gag cct gag caa gcc gct gcc tcc aat    171
          Met Cys Pro Ser Cys Glu Pro Glu Gln Ala Ala Ala Ser Asn
          1               5                   10

ggc aat gcg aac ggc aat ggc gcc tcc aat ggc aat gga aac cac gac      219
Gly Asn Ala Asn Gly Asn Gly Ala Ser Asn Gly Asn Gly Asn His Asp
15                  20                  25                  30

gga atg act ggt att gag act cgc caa gca caa aac gca cgc tac cag      267
Gly Met Thr Gly Ile Glu Thr Arg Gln Ala Gln Asn Ala Arg Tyr Gln
                35                  40                  45

cca tca cgg aat ccc tac cag ccc gtc ggt gac ttt ttg tcc aac gtg      315
Pro Ser Arg Asn Pro Tyr Gln Pro Val Gly Asp Phe Leu Ser Asn Val
            50                  55                  60
```

-continued

```
aac aac ttc aag atc att gag agc acc ctg cga gag ggc gag cag ttc      363
Asn Asn Phe Lys Ile Ile Glu Ser Thr Leu Arg Glu Gly Glu Gln Phe
        65                  70                  75

gcc aat gcc ttc ttc gac acg gtgagtcaag ccacatcgca agcaaatact         414
Ala Asn Ala Phe Phe Asp Thr
    80                  85

tgctcctcac aacggccgca agcctgggct actttggtag ctcggcggtg tttttgctgt    474

cgatgtgtcc tggcggcatc ccggcgcaaa aacagacctc atagactgac tcatgctttt    534

tttaacctcc gcgcag gcc aag aag att gag atc gcc aag gcg ctg gac gac    586
                  Ala Lys Lys Ile Glu Ile Ala Lys Ala Leu Asp Asp
                                  90                  95

ttt ggc gtc gac tac atc gag ctc acc agc ccg gct gcc tcg gag cag      634
Phe Gly Val Asp Tyr Ile Glu Leu Thr Ser Pro Ala Ala Ser Glu Gln
        100                 105                 110

tcc agg ctt gac tgc gct gcc atc tgc aag ctg gga ctc aag gcc aag      682
Ser Arg Leu Asp Cys Ala Ala Ile Cys Lys Leu Gly Leu Lys Ala Lys
    115                 120                 125

atc ctc acc cac atc agg tgc cac atg gac gac gcg cgc atc gcc gtc      730
Ile Leu Thr His Ile Arg Cys His Met Asp Asp Ala Arg Ile Ala Val
130                 135                 140                 145

gag acc ggt gtt gac ggc gtc gac att gtc atc ggc acc tct tcg ttc      778
Glu Thr Gly Val Asp Gly Val Asp Ile Val Ile Gly Thr Ser Ser Phe
                150                 155                 160

ctc atg gag cac tcg cac ggc aag gac atg acc tac atc acc aac acg      826
Leu Met Glu His Ser His Gly Lys Asp Met Thr Tyr Ile Thr Asn Thr
            165                 170                 175

gcc att gag gtc atc aac ttt gtc aag agc aag ggc atc gag gtc cgc      874
Ala Ile Glu Val Ile Asn Phe Val Lys Ser Lys Gly Ile Glu Val Arg
        180                 185                 190

ttc tca tcc gag gac tcg ttc cgc agc aac ctg gtt gac ctg ctg agc      922
Phe Ser Ser Glu Asp Ser Phe Arg Ser Asn Leu Val Asp Leu Leu Ser
    195                 200                 205

atc tac tcg acc gtc gac aag att ggt gtc aac cgt gtc ggt att gct      970
Ile Tyr Ser Thr Val Asp Lys Ile Gly Val Asn Arg Val Gly Ile Ala
210                 215                 220                 225

gat acc gtc ggt tgc gcc tcg ccc cgc cag gtc tac gac ctg gtc aag     1018
Asp Thr Val Gly Cys Ala Ser Pro Arg Gln Val Tyr Asp Leu Val Lys
                230                 235                 240

acc ctg cgt ggt gtt gtc tct tg  gtgagccaca ggtctgatga atcttgtgct    1071
Thr Leu Arg Gly Val Val Ser Cys
            245

gcttggtgct gatgctaaca gttcgatag t gac att gag aca cac ttc cac aac   1125
                                  Asp Ile Glu Thr His Phe His Asn
                                  250                 255

gac act ggc tgt gcc atc tca aat gct ttt tgc gct ttg gag gcc ggt     1173
Asp Thr Gly Cys Ala Ile Ser Asn Ala Phe Cys Ala Leu Glu Ala Gly
        260                 265                 270

gct acc cac atc gac acg tgt gtc ctg ggt atc ggc gag cgt aac gga     1221
Ala Thr His Ile Asp Thr Cys Val Leu Gly Ile Gly Glu Arg Asn Gly
    275                 280                 285

att acc cct ctt gga ggt ctg atg gct cgc atg att gtc ggc tcc aag     1269
Ile Thr Pro Leu Gly Gly Leu Met Ala Arg Met Ile Val Gly Ser Lys
290                 295                 300                 305

gac tac gtt ctg agc aag tac aag ctg cac aag ctc aag gac att gag     1317
Asp Tyr Val Leu Ser Lys Tyr Lys Leu His Lys Leu Lys Asp Ile Glu
                310                 315                 320

gag ctt gtt gcc gac gcc gtt cag gtc aac at  gtaagttttg ccatcccagt   1369
Glu Leu Val Ala Asp Ala Val Gln Val Asn Ile
```

-continued

```
            325                 330

gcagttttca ttctgggtag gattgctaac attttgtctc tgtag t cct ttc aat     1424
                                                    Pro Phe Asn
                                                            335

aac tac atc act ggt ttc tgt gct ttc acc cac aa  gtatgttccg          1469
Asn Tyr Ile Thr Gly Phe Cys Ala Phe Thr His Lys
                340                 345

tcacacactg gtatctacta ttgattcaaa actaactcgt tgctatag g gcc ggt      1524
                                                       Ala Gly

atc cat gcc aag gct att ctc aag aac ccc tca aca tat gag att att     1572
Ile His Ala Lys Ala Ile Leu Lys Asn Pro Ser Thr Tyr Glu Ile Ile
350                 355                 360                 365

gtatgttttt gatctgttca cgcactgtgc cagcatgggt atgatgagcc gaaaatacta   1632

acccttgatt aatcag gac ccg act ctg ttc ggc atc act cgc tat gtc cac   1684
                  Asp Pro Thr Leu Phe Gly Ile Thr Arg Tyr Val His
                                  370                 375

ttc gcc agc aga ttg acg gga tgg aac gca atc aag agc aga gca tcg     1732
Phe Ala Ser Arg Leu Thr Gly Trp Asn Ala Ile Lys Ser Arg Ala Ser
        380                 385                 390

cag ctc aac att gag atg acg gat gag cag tgc aag gag tgc act gcc     1780
Gln Leu Asn Ile Glu Met Thr Asp Glu Gln Cys Lys Glu Cys Thr Ala
    395                 400                 405

aag atc aag ctg ttg gct gac att agg ccg atc gct atc gac gac gcc     1828
Lys Ile Lys Leu Leu Ala Asp Ile Arg Pro Ile Ala Ile Asp Asp Ala
410                 415                 420                 425

gac tcc atc att cac gca ttc cac cgc agc atc aac tcg ggc cag cct     1876
Asp Ser Ile Ile His Ala Phe His Arg Ser Ile Asn Ser Gly Gln Pro
                430                 435                 440

att cag tat ctc gga agc ctg ctc ccc aac atg acg gag gag gag aag     1924
Ile Gln Tyr Leu Gly Ser Leu Leu Pro Asn Met Thr Glu Glu Glu Lys
            445                 450                 455

gcc gcc ctg gca gat gta gag cgc cgt gag tcg aac gat gcc gag caa     1972
Ala Ala Leu Ala Asp Val Glu Arg Arg Glu Ser Asn Asp Ala Glu Gln
        460                 465                 470

ccg gcg gcc aag agg gcc aag gtc gag gct gtt gca t gagcacaacg        2019
Pro Ala Ala Lys Arg Ala Lys Val Glu Ala Val Ala
    475                 480                 485

gaatttttga gcattgtcga agcgtgagcg agtcacatat atattgttga cgcagaattt   2079

tggtggtcaa agggaagtac agaaaggcct tgggctttga ttttcctaac cccaaagcgt   2139

tgacattttt attatgtctt cttctgtctg catacgaagt caaaaaagga aggagaaagg   2199

aaaagtatcg tcaggatggg atggtttacg gatctacatt ggtaccggag ctattcaagg   2259

atagattgtg tttgctttga tttgccccca tggatgagtt ggggcctttt gctgatttgc   2319

tatatgttgc tataccattg aatgaaa                                       2346


<210> SEQ ID NO 3
<211> LENGTH: 449
<212> TYPE: PRT
<213> ORGANISM: Magnaporthe grisea

<400> SEQUENCE: 3

Met Cys Pro Ser Cys Glu Pro Glu Gln Ala Ala Ala Ser Asn Gly Asn
1               5                   10                  15

Ala Asn Gly Asn Gly Ala Ser Asn Gly Asn Gly Asn His Asp Gly Met
            20                  25                  30

Thr Gly Ile Glu Thr Arg Gln Ala Gln Asn Ala Arg Tyr Gln Pro Ser
        35                  40                  45
```

-continued

```
Arg Asn Pro Tyr Gln Pro Val Gly Asp Phe Leu Ser Asn Val Asn Asn
    50                  55                  60

Phe Lys Ile Ile Glu Ser Thr Leu Arg Glu Gly Glu Gln Phe Ala Asn
65                  70                  75                  80

Ala Phe Phe Asp Thr Ala Lys Lys Ile Glu Ile Ala Lys Ala Leu Asp
                85                  90                  95

Asp Phe Gly Val Asp Tyr Ile Glu Leu Thr Ser Pro Ala Ala Ser Glu
            100                 105                 110

Gln Ser Arg Leu Asp Cys Ala Ala Ile Cys Lys Leu Gly Leu Lys Ala
        115                 120                 125

Lys Ile Leu Thr His Ile Arg Cys His Met Asp Asp Ala Arg Ile Ala
    130                 135                 140

Val Glu Thr Gly Val Asp Gly Val Asp Ile Val Ile Gly Thr Ser Ser
145                 150                 155                 160

Phe Leu Met Glu His Ser His Gly Lys Asp Met Thr Tyr Ile Thr Asn
                165                 170                 175

Thr Ala Ile Glu Val Ile Asn Phe Val Lys Ser Lys Gly Ile Glu Val
            180                 185                 190

Arg Phe Ser Ser Glu Asp Ser Phe Arg Ser Asn Leu Val Asp Leu Leu
        195                 200                 205

Ser Ile Tyr Ser Thr Val Asp Lys Ile Gly Val Asn Arg Val Gly Ile
    210                 215                 220

Ala Asp Thr Val Gly Cys Ala Ser Pro Arg Gln Val Tyr Asp Leu Val
225                 230                 235                 240

Lys Thr Leu Arg Gly Val Val Ser Cys Asp Ile Glu Thr His Phe His
                245                 250                 255

Asn Asp Thr Gly Cys Ala Ile Ser Asn Ala Phe Cys Ala Leu Glu Ala
            260                 265                 270

Gly Ala Thr His Ile Asp Thr Cys Val Leu Gly Ile Gly Glu Arg Asn
        275                 280                 285

Gly Ile Thr Pro Leu Gly Gly Leu Met Ala Arg Met Ile Val Gly Ser
    290                 295                 300

Lys Asp Tyr Val Leu Ser Lys Tyr Lys Leu His Lys Leu Lys Asp Ile
305                 310                 315                 320

Glu Glu Leu Val Ala Asp Ala Val Gln Val Asn Ile Pro Phe Asn Asn
                325                 330                 335

Tyr Ile Thr Gly Phe Cys Ala Phe Thr His Lys Ala Gly Ile His Ala
            340                 345                 350

Lys Ala Ile Leu Lys Asn Pro Ser Thr Tyr Glu Ile Ile Asp Pro Thr
        355                 360                 365

Leu Phe Gly Ile Thr Arg Tyr Val His Phe Ala Ser Arg Leu Thr Gly
    370                 375                 380

Trp Asn Ala Ile Lys Ser Arg Ala Ser Gln Leu Asn Ile Glu Met Thr
385                 390                 395                 400

Asp Glu Gln Cys Lys Glu Cys Thr Ala Lys Ile Lys Leu Leu Ala Asp
                405                 410                 415

Ile Arg Pro Ile Ala Ile Asp Asp Ala Asp Ser Ile Ile His Ala Phe
            420                 425                 430

His Arg Ser Ile Asn Ser Gly Gln Pro Ile Gln Ser Leu Gly Ser Leu
        435                 440                 445

Leu
```

METHODS FOR THE IDENTIFICATION OF INHIBITORS OF HOMOCITRATE SYNTHASE AS ANTIBIOTICS

The invention relates generally to methods for the identification of antibiotics, preferably anti fungals that affect the biosynthesis of lysine. This application is with U.S. application Ser. No. 10/011146, filed 11/9/2001, entitled "Methods for the Identification of Inhibitors of α-Aminoadipate Reductase as Antibiotics".

FIELD OF THE INVENTION

BACKGROUND OF THE INVENTION

Filamentous fungi are the causal agents responsible for many serious pathogenic infections of plants and animals. Since fungi are eukaryotes, and thus more similar to their host organisms than, for example bacteria, the treatment of infections by fungi poses special risks and challenges not encountered with other types of infections. One such fungus is *Magnaporthe grisea*, the fungus that causes rice blast disease. It is an organism that poses a significant threat to food supplies worldwide. Other examples of plant pathogens of economic importance include the pathogens in the genera Agaricus, Alternaria, Anisogramma, Anthracoidea, Antrodia, Apiognomonia, Apiosporina, Armillaria, Ascochyta, Aspergillus, Bipolaris, Bjerkandera, Botryosphaeria, Botrytis, Ceratobasidium, Ceratocystis, Cercospora, Cercosporidium, Cerotelium, Cerrena, Chondrostereum, Chryphonectria, Chrysomyxa, Cladosporium, Claviceps, Cochliobolus, Coleosporium, Colletotrichium, Colletotrichum, Corticium, Corynespora, Cronartium, Cryphonectria, Cryptosphaeria, Cyathus, Cymadothea, Cytospora, Daedaleopsis, Diaporthe, Didymella, Diplocarpon, Diplodia, Discohainesia, Discula, Dothistroma, Drechslera, Echinodontium, Elsinoe, Endocronartium, Endothia, Entyloma, Epichloe, Erysiphe, Exobasidium, Exserohilum, Fomes, Fomitopsis, Fusarium, Gaeumannomyces, Ganoderma, Gibberella, Gloeocercospora, Gloeophyllum, Gloeoporus, Glomerella, Gnomoniella, Guignardia, Gymnosporangium, Helminthosporium, Herpotrichia, Heterobasidion, Hirschioporus, Hypodermella, Inonotus, Irpex, Kabatiella, Kabatina, Laetiporus, Laetisaria, Lasiodiplodia, Laxitextum, Leptographium, Leptosphaeria, Leptosphaerulina, Leucytospora, Linospora, Lophodermella, Lophodermium, Macrophomina, Magnaporthe, Marssonina, Melampsora, Melampsorella, Meria, Microdochium, Microsphaera, Monilinia, Monochaetia, Morchella, Mycosphaerella, Myrothecium, Nectria, Nigrospora, Ophiosphaerella, Ophiostoma, Penicillium, Perenniporia, Peridermium, Pestalotia, Phaeocryptopus, Phaeolus, Phakopsora, Phellinus, Phialophora, Phoma, Phomopsis, Phragmidium, Phyllachora, Phyllactinia, Phyllosticta, Phymatotrichopsis, Pleospora, Podosphaera, Pseudopeziza, Pseudoseptoria, Puccinia, Pucciniastrum, Pyricularia, Rhabdocline, Rhizoctonia, Rhizopus, Rhizosphaera, Rhynchosporium, Rhytisma, Schizophyllum, Schizopora, Scirrhia, Sclerotinia, Sclerotium, Scytinostroma, Septoria, Setosphaera, Sirococcus, Spaerotheca, Sphaeropsis, Sphaerotheca, Sporisorium, Stagonospora, Stemphylium, Stenocarpella, Stereum, Taphrina, Thielaviopsis, Tilletia, Trametes, Tranzschelia, Trichoderma, Tubakia, Typhula, Uncinula, Urocystis, Uromyces, Ustilago, Valsa, Venturia, Verticillium, Xylaria, and others. Related organisms in the classification, oomycetes, that include the genera Albugo, Aphanomyces, Bremia, Peronospora, Phytophthora, Plasmodiophora, Plasmopara, Pseudoperonospora, Pythium, Sclerophthora, and others are also significant plant pathogens and are sometimes classified along with the true fungi. Human diseases that are caused by filamentous fungi include life-threatening lung and disseminated diseases, often a result of infections by *Aspergillus fumigatus*. Other fungal diseases in animals are caused by fungi in the genera, Fusarium, Blastomyces, Microsporum, Trichophyton, Epidermophyton, Candida, Histoplamsa, Pneumocystis, Cryptococcus, other Aspergilli, and others. The control of fungal diseases in plants and animals is usually mediated by chemicals that inhibit the growth, proliferation, and/or pathogenicity of the fungal organisms. To date, there are less than twenty known modes-of-action for plant protection fungicides and human antifungal compounds.

A pathogenic organism has been defined as an organism that causes, or is capable of causing disease. Pathogenic organisms propagate on or in tissues and may obtain nutrients and other essential materials from their hosts. A substantial amount of work concerning filamentous fungal pathogens has been performed with the human pathogen, *Aspergillus fumigatus*. Shibuya et al. (Shibuya, K., M. Takaoka, et al. (1999) Microb Pathog 27: 123–31 (PMID: 10455003)) have shown that the deletion of either of two suspected pathogenicity related genes encoding an alkaline protease or a hydrophobin (rodlet) respectively, did not reduce mortality of mice infected with these mutant strains. Smith et al. (Smith, J. M., C. M. Tang, et al. (1994) Infect Immun 62: 5247–54 (PMID: 7960101)) showed similar results with alkaline protease and the ribotoxin restrictocin; *Aspergillus fumigatus* strains mutated for either of these genes were fully pathogenic to mice. Reichard et al. (Reichard, U., M. Monod, et al. (1997) J Med Vet Mycol 35: 189–96 (PMID: 9229335)) showed that deletion of the suspected pathogenicity gene encoding, aspergillopepsin (PEP) in *Aspergillus fumigatus*, had no effect on mortality in a guinea pig model system, and Aufauvre-Brown et al (Aufauvre-Brown, A., E. Mellado, et al. (1997) Fungal Genet Biol 21: 141–52 (PMID: 9073488)) showed no effects of a chitin synthase mutation on pathogenicity. However, not all experiments produced negative results. Ergosterol is an important membrane component found in fungal organisms. Pathogenic fungi that lack key enzymes in this biochemical pathway might be expected to be non-pathogenic since neither the plant nor animal hosts contain this particular sterol. Many antifungal compounds that affect this biochemical pathway have been described (Onishi, J. C. and A. A. Patchett (1990a, b, c, d, and e) U.S. Pat. Nos. 4,920,109; 4,920,111; 4,920,112; 4,920,113; and 4,921,844, Merck & Co. Inc. (Rahway N.J.)) and (Hewitt, H. G. (1998) *Fungicides in Crop Protection* Cambridge, University Press). D'Enfert et al. (D'Enfert, C., M. Diaquin, et al. (1996) Infect Immun 64: 4401–5 (PMID: 8926121)) showed that an *Aspergillus fumigatus* strain mutated in an orotidine 5'-phosphate decarboxylase gene was entirely non-pathogenic in mice, and Brown et al. (Brown, J. S., A. Aufauvre-Brown, et al. (2000) Mol Microbiol 36:1371–80 (PMID: 10931287)) observed a non-pathogenic result when genes involved in the synthesis of para-aminobenzoic acid were mutated. Some specific target genes have been described as having utility for the screening of inhibitors of plant pathogenic fungi. Bacot et al. (Bacot, K. O., D. B. Jordan, et al. (2000) U.S. Pat. No. 6,074,830, E. I. du Pont de Nemours & Company (Wilmington Del.)) describe the use of 3,4-dihydroxy-2-butanone 4-phosphate synthase, and Davis et al. (Davis, G. E., G. D. Gustafson, et al. (1999) U.S. Pat. No. 5,976,848, Dow AgroSciences LLC (Indianapolis Ind.)) describe the use of dihydroorotate dehydrogenase for potential screening purposes.

There are also a number of papers that report less clear results, showing neither full pathogenicity nor non-pathogenicity of mutants. Hensel et al. (Hensel, M., H. N. Arst, Jr., et al. (1998) Mol Gen Genet 258: 553–7 (PMID: 9669338)) showed only moderate effects of the deletion of the areA transcriptional activator on the pathogenicity of *Aspergillus fumigatus*. Tang et al. (Tang, C. M., J. M. Smith, et al. (1994) Infect Immun 62: 5255–60 (PMID: 7960102)) using the related fungus, *Aspergillus nidulans*, observed that a mutation in para-aminobenzoic acid synthesis prevented mortality in mice, while a mutation in lysine biosynthesis had no significant effect on the mortality of the infected mice.

Therefore, it is not currently possible to determine which specific growth materials may be readily obtained by a pathogen from its host, and which materials may not. Surprising, especially in light of the results showing that a lysine biosynthesis mutation in the filamentous fungus, *Aspergillus nidulans*, had no significant effect on the pathogenicity in a mouse model system (Tang, C. M., J. M. Smith, et al. (1994) Infect Immun 62: 5255–60 (PMID: 7960102)), we have found that *Magnaporthe grisea* that cannot synthesize their own lysine are entirely non-pathogenic on their host organism. To date there do not appear to be any publications demonstrating an anti-pathogenic effect of the knock-out, over-expression, antisense expression, or inhibition of the genes or gene products involved in lysine biosynthesis in filamentous fungi. Thus, it has not been shown that the de novo biosynthesis of lysine is essential for fungal pathogenicity. Our co-pending application entitled "Methods for the Identification of Inhibitors of α-Aminoadipate Reductase as Antibiotics" shows that the disruption of lysine biosynthesis as the result of a disruption of the gene encoding the enzyme activity, alpha-aminoadipate-semialdehyde dehydrogenase, also results in a non-pathogenic phenotype for *M. grisea*. Thus, it would be desirable to determine the utility of the enzymes involved in lysine biosynthesis for evaluating antibiotic compounds, especially fungicides. If a fungal biochemical pathway or specific gene product in that pathway is shown to be required for fungal pathogenicity, various formats of in vitro and in vivo screening assays may be put in place to discover classes of chemical compounds that react with the validated target gene, gene product, or biochemical pathway, and are thus candidates for antifungal, biocide, and biostatic materials.

SUMMARY OF THE INVENTION

Surprisingly, the present inventors have discovered that in vivo disruption of the gene encoding homocitrate synthase in *Magnaporthe grisea* prevents or inhibits the pathogenicity of the fungus. Thus, the present inventors have discovered that homocitrate synthase is essential for normal rice blast pathogenicity, and can be used as a target for the identification of antibiotics, preferably fungicides. Accordingly, the present invention provides methods for the identification of compounds that inhibit homocitrate synthase expression or activity. The methods of the invention are useful for the identification of antibiotics, preferably fungicides.

DETAILED DESCRIPTION OF THE INVENTION

Figure 1:
FIG. 1 shows the reaction performed by the homocitrate synthase (HCS1) reaction. The Substrates/Products are Acetyl CoA+$H_2O$+2-oxoglutarate and the Products/Substrates are 2-hydroxybutane-1,2,4-tricarboxylate+CoA. The function of the homocitrate synthase enzyme is the interconversion of Acetyl CoA, 2-oxoglutarate, and $H_2O$ to 2-hydroxybutane-1,2,4-tricarboxylate and CoA. This reaction is part of the lysine biosynthesis pathway.

Unless otherwise indicated, the following terms are intended to have the following meanings in interpreting the present invention.

The term "active against" in the context of compounds, agents, or compositions having antibiotic activity indicates that the compound exerts an effect on a particular target or targets which is deleterious to the in vitro and/or in vivo growth of an organism having that target or targets. In particular, a compound active against a gene exerts an action on a target which affects an expression product of that gene. This does not necessarily mean that the compound acts directly on the expression product of the gene, but instead indicates that the compound affects the expression product in a deleterious manner. Thus, the direct target of the compound may be, for example, at an upstream component which reduces transcription from the gene, resulting in a lower level of expression. Likewise, the compound may affect the level of translation of a polypeptide expression product, or may act on a downstream component of a biochemical pathway in which the expression product of the gene has a major biological role. Consequently, such a compound can be said to be active against the gene, against the gene product, or against the related component either upstream or downstream of that gene or expression product. While the term "active against" encompasses a broad range of potential activities, it also implies some degree of specificity of target. Therefore, for example, a general protease is not "active against" a particular gene which produces a polypeptide product. In contrast, a compound which inhibits a particular enzyme is active against that enzyme and against the gene which codes for that enzyme.

As used herein, the term "allele" refers to any of the alternative forms of a gene that may occur at a given locus.

The term "antibiotic" refers to any substance or compound that when contacted with a living cell, organism, virus, or other entity capable of replication, results in a reduction of growth, viability, or pathogenicity of that entity.

The term "binding" refers to a non-covalent or a covalent interaction, preferably non-covalent, that holds two molecules together. For example, two such molecules could be an enzyme and an inhibitor of that enzyme. Non-covalent interactions include hydrogen bonding, ionic interactions among charged groups, van der Waals interactions and hydrophobic interactions among nonpolar groups. One or more of these interactions can mediate the binding of two molecules to each other.

The term "biochemical pathway" or "pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene.

As used herein, the term "cDNA" means complementary deoxyribonucleic acid.

As used herein, the term "CoA" means coenzyme A.

As used herein, the term "conditional lethal" refers to a mutation permitting growth and/or survival only under special growth or environmental conditions.

As used herein, the term "cosmid" refers to a hybrid vector, used in gene cloning, that includes a cos site (from the lambda bacteriophage). It also contains drug resistance marker genes and other plasmid genes. Cosmids are especially suitable for cloning large genes or multigene fragments.

As used herein, the term "dominant allele" refers to a dominant mutant allele in which a discernable mutant phenotype can be detected when this mutation is present in an organism that also contains a wild type (non-mutant), recessive allele, or other dominant allele.

As used herein, the term "DNA" means deoxyribonucleic acid.

As used herein, the term "ELISA" means enzyme-linked immunosorbent assay.

"Fungi" (singular: fungus) refers to whole fungi, fungal organs and tissues (e.g., asci, hyphae, pseudohyphae, rhizoid, sclerotia, sterigmata, spores, sporodochia, sporangia, synnemata, conidia, ascostroma, cleistothecia, mycelia, perithecia, basidia and the like), spores, fungal cells and the progeny thereof. Fungi are a group of organisms (about 50,000 known species), including, but not limited to, mushrooms, mildews, moulds, yeasts, etc., comprising the kingdom Fungi. They can either exist as single cells or make up a multicellular body called a mycelium, which consists of filaments known as hyphae. Most fungal cells are multinucleate and have cell walls, composed chiefly of chitin. Fungi exist primarily in damp situations on land and, because of the absence of chlorophyll and thus the inability to manufacture their own food by photosynthesis, are either parasites on other organisms or saprotrophs feeding on dead organic matter. The principal criteria used in classification are the nature of the spores produced and the presence or absence of cross walls within the hyphae. Fungi are distributed worldwide in terrestrial, freshwater, and marine habitats. Some live in the soil. Many pathogenic fungi cause disease in animals and man or in plants, while some saprotrophs are destructive to timber, textiles, and other materials. Some fungi form associations with other organisms, most notably with algae to form lichens.

As used herein, the term "fungicide", "antifungal", or "antimycotic" refers to an antibiotic substance or compound that kills or suppresses the growth, viability, or pathogenicity of at least one fungus, fungal cell, fungal tissue or spore.

In the context of this disclosure, "gene" should be understood to refer to a unit of heredity. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the similar way in referring to RNA chains, linear chains made of ribonucleotides.) The gene may include regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different fungal strains, or even within a particular fungal strain, without altering the identity of the gene.

As used in this disclosure, the terms "growth" or "cell growth" of an organism refers to an increase in mass, density, or number of cells of said organism. Some common methods for the measurement of growth include the determination of the optical density of a cell suspension, the counting of the number of cells in a fixed volume, the counting of the number of cells by measurement of cell division, and the measurement of cellular mass or cellular volume.

As used in this disclosure, the term "growth conditional phenotype" indicates that a fungal strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a fungal strain having a heat-sensitive phenotype) exhibits significantly different growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes.

As used herein, the term "$H_2$" means water.

As used herein, the term "HCS1" means a gene encoding homocitrate synthase activity, referring to an enzyme that catalyses the interconversion of acetyl-CoA, $H_2O$, and 2-oxoglutarate with 2-hydroxybutane-1,2,4-tricarboxylate and CoA.

As used herein, the term "heterologous HCS1 gene" means a gene, not derived from *Magnaporthe grisea*, and having: at least 50% sequence identity, preferably 60%, 70%, 80%, 90%, 95%, 99% sequence identity and each integer unit of sequence identity from 50–100% in ascending order to SEQ ID NO: 1 or SEQ ID NO: 2; or at least 10% of the activity of a *Magnaporthe grisea* homocitrate synthase, preferably 25%, 50%, 75%, 90%, 95%, 99% and each integer unit of activity from 10–100% in ascending order.

As used herein, the term "homocitrate synthase (EC 4.1.3.21) or homocitrate synthase polypeptide" is synonymous with "the HCS1 gene product" and refers to an enzyme that catalyses the interconversion of acetyl-CoA, $H_2O$, and 2-oxoglutarate with 2-hydroxybutane-1,2,4-tricarboxylate and CoA.

As used herein, the term "His-Tag" refers to an encoded polypeptide consisting of multiple consecutive histidine amino acids.

As used herein, the term "HPLC" means high pressure liquid chromatography.

As used herein, the terms "hph", "hygromycin B phosphotransferase", and "hygromycin resistance gene" refer to the *E. coli* hygromycin phosphotransferase gene or gene product.

As used herein, the term "hygromycin B" refers to an aminoglycosidic antibiotic, used for selection and maintenance of eukaryotic cells containing the *E. coli* hygromycin resistance gene.

"Hypersensitive" refers to a phenotype in which cells are more sensitive to antibiotic compounds than are wild-type cells of similar or identical genetic background.

"Hyposensitive" refers to a phenotype in which cells are less sensitive to antibiotic compounds than are wild-type cells of similar or identical genetic background.

As used herein, the term "imperfect state" refers to a classification of a fungal organism having no demonstrable sexual life stage.

The term "inhibitor", as used herein, refers to a chemical substance that inactivates the enzymatic activity of homocitrate synthase or substantially reduces the level of enzymatic activity, wherein "substantially" means a reduction at least as great as the standard deviation for a measurement, preferably a reduction by 50%, more preferably a reduction of at least one magnitude, i.e. to 10%. The inhibitor may function by interacting directly with the enzyme, a cofactor of the enzyme, the substrate of the enzyme, or any combination thereof.

A polynucleotide may be "introduced" into a fungal cell by any means known to those of skill in the art, including transfection, transformation or transduction, transposable element, electroporation, particle bombardment, and infection. The introduced polynucleotide may be maintained in the cell stably if it is incorporated into a non-chromosomal autonomous replicon or integrated into the fungal chromosome. Alternatively, the introduced polynucleotide may be present on an extra-chromosomal non-replicating vector and be transiently expressed or transiently active.

As used herein, the term "knockout" or "gene disruption" refers to the creation of organisms carrying a null mutation (a mutation in which there is no active gene product), a partial null mutation or mutations, or an alteration or alterations in gene regulation by interrupting a DNA sequence through insertion of a foreign piece of DNA. Usually the foreign DNA encodes a selectable marker.

As used herein, the term "LB agar" means Luria's Broth agar.

The term "method of screening" means that the method is suitable, and is typically used, for testing for a particular property or effect in a large number of compounds. Typically, more than one compound is tested simultaneously (as in a 96-well microtiter plate), and preferably significant portions of the procedure can be automated. "method of screening" also refers to determining a set of different properties or effects of one compound simultaneously.

As used herein, the term "mRNA" means messenger ribonucleic acid.

As used herein, the term "mutant form" of a gene refers to a gene which has been altered, either naturally or artificially, changing the base sequence of the gene. The change in the base sequence may be of several different types, including changes of one or more bases for different bases, deletions, and/or insertions, such as by a transposon. By contrast, a normal form of a gene (wild type) is a form commonly found in natural populations of an organism. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the strain having that gene, while a mutant form of a gene suitable for use in these methods does provide such a growth conditional phenotype.

As used herein, the term "Ni" refers to nickel.

As used herein, the term "Ni-NTA" refers to nickel sepharose.

As used herein, the term "one form" of a gene is synonymous with the term "gene", and a "different form" of a gene refers to a gene that has greater than 49% sequence identity and less than 100% sequence identity with said first form.

As used herein, the term "pathogenicity" refers to a capability of causing disease. The term is applied to parasitic microorganisms in relation to their hosts.

As used herein, the term "PCR" means polymerase chain reaction.

The "percent (%) sequence identity" between two polynucleotide or two polypeptide sequences is determined according to the either the BLAST program (Basic Local Alignment Search Tool; (Altschul, S. F., W. Gish, et al. (1990) J Mol Biol 215: 403–10 (PMID: 2231712)) at the National Center for Biotechnology or using Smith Waterman Alignment (Smith, T. F. and M. S. Waterman (1981) J Mol Biol 147:195–7 (PMID: 7265238)) as incorporated into GeneMatcher Plus™. It is understood that for the purposes of determining sequence identity when comparing a DNA sequence to an RNA sequence, a thymine nucleotide is equivalent to a uracil nucleotide.

By "polypeptide" is meant a chain of at least two amino acids joined by peptide bonds. The chain may be linear, branched, circular or combinations thereof. Preferably, polypeptides are from about 10 to about 1000 amino acids in length, more preferably 10–50 amino acids in length. The polypeptides may contain amino acid analogs and other modifications, including, but not limited to glycosylated or phosphorylated residues.

As used herein, the term "proliferation" is synonymous to the term "growth".

As used herein, the term "reverse transcriptase-PCR" means reverse transcription-polymerase chain reaction.

As used herein, the term "RNA" means ribonucleic acid.

As used herein, "semi-permissive conditions" are conditions in which the relevant culture parameter for a particular growth conditional phenotype is intermediate between permissive conditions and non-permissive conditions. Consequently, in semi-permissive conditions an organism having a growth conditional phenotype will exhibit growth rates intermediate between those shown in permissive conditions and non-permissive conditions. In general, such intermediate growth rate may be due to a mutant cellular component which is partially functional under semi-permissive conditions, essentially fully functional under permissive conditions, and is non-functional or has very low function under non-permissive conditions, where the level of function of that component is related to the growth rate of the organism. An intermediate growth rate may also be a result of a nutrient substance or substances that are present in amounts not sufficient for optimal growth rates to be achieved.

"Sensitivity phenotype" refers to a phenotype that exhibits either hypersensitivity or hyposensitivity.

The term "specific binding" refers to an interaction between homocitrate synthase and a molecule or compound, wherein the interaction is dependent upon the primary amino acid sequence and/or the conformation of homocitrate synthase.

As used herein, the term "TLC" means thin layer chromatography.

"Transform", as used herein, refers to the introduction of a polynucleotide (single or double stranded DNA, RNA, or a combination thereof) into a living cell by any means. Transformation may be accomplished by a variety of methods, including, but not limited to, electroporation, polyethylene glycol mediated uptake, particle bombardment, agrotransformation, and the like. This process may result in transient or stable expression of the transformed polynucleotide. By "stably transformed" is meant that the sequence of interest is integrated into a replicon in the cell, such as a chromosome or episome. Transformed cells encompass not only the end product of a transformation process, but also the progeny thereof which retain the polynucleotide of interest.

For the purposes of the invention, "transgenic" refers to any cell, spore, tissue or part, that contains all or part of at least one recombinant polynucleotide. In many cases, all or part of the recombinant polynucleotide is stably integrated into a chromosome or stable extra-chromosomal element, so that it is passed on to successive generations.

As used herein, the term "transposase" refers to an enzyme that catalyzes transposition. Preferred transposons are described in WO 00/55346, PCT/US00/07317, and U.S. Ser. No. 09/658859.

As used herein, the term "transposition" refers to a complex genetic rearrangement process involving the movement or copying of a polynucleotide (transposon) from one location and insertion into another, often within or between a genome or genomes, or DNA constructs such as plasmids, bacmids, and cosmids.

As used herein, the term "transposon" (also known as a "transposable element", "transposable genetic element", "mobile element", or "jumping gene") refers to a mobile DNA element such as those, for example, described in WO 00/55346, PCT/US00/07317, and U.S. Ser. No. 09/658859. Transposons can disrupt gene expression or cause deletions and inversions, and hence affect both the genotype and phenotype of the organisms concerned. The mobility of transposable elements has long been used in genetic manipulation, to introduce genes or other information into the genome of certain model systems.

As used herein, the term "Tween 20" means sorbitan mono-9-octadecenoate poly(oxy-1,1-ethanediyl).

As used in this disclosure, the term "viability" of an organism refers to the ability of an organism to demonstrate growth under conditions appropriate for said organism, or to demonstrate an active cellular function. Some examples of active cellular functions include respiration as measured by gas evolution, secretion of proteins and/or other compounds, dye exclusion, mobility, dye oxidation, dye reduction, pigment production, changes in medium acidity, and the like.

The present inventors have discovered that disruption of the HCS1 gene and/or gene product inhibits the pathogenicity of *Magnaporthe grisea*. Thus, the inventors are the first to demonstrate that homocitrate synthase is a target for antibiotics, preferably antifungals.

Accordingly, the invention provides methods for identifying compounds that inhibit HCS1 gene expression or biological activity of its gene product(s). Such methods include ligand binding assays, assays for enzyme activity, cell-based assays, and assays for HCS1 gene expression. Any compound that is a ligand for homocitrate synthase may have antibiotic activity. For the purposes of the invention, "ligand" refers to a molecule that will bind to a site on a polypeptide. The compounds identified by the methods of the invention are useful as antibiotics.

Thus, in one embodiment, the invention provides a method for identifying a test compound as a candidate for an antibiotic, comprising:

a) contacting a homocitrate synthase polypeptide with said test compound; and b) detecting the presence or absence of binding between said test compound and said homocitrate synthase polypeptide;

wherein binding indicates that said test compound is a candidate for an antibiotic.

The homocitrate synthase protein may have the amino acid sequence of a naturally occurring homocitrate synthase found in a fungus, animal, plant, or microorganism, or may have an amino acid sequence derived from a naturally occurring sequence. Preferably the homocitrate synthase is a fungal homocitrate synthase. The cDNA (SEQ ID NO: 1) encoding the homocitrate synthase protein, the genomic DNA (SEQ ID NO: 2) encoding the protein, and the polypeptide (SEQ ID NO: 3) can be found herein.

By "fungal homocitrate synthase" is meant an enzyme that can be found in at least one fungus, and which catalyzes the interconversion of acetyl-CoA and $H_2O$ and 2-oxoglutarate with 2-hydroxybutane-1,2,4-tricarboxylate and CoA. The homocitrate synthase may be from any of the fungi, including ascomycota, zygomycota, basidiomycota, chytridiomycota, and lichens.

In one embodiment, the homocitrate synthase is a Magnaporthe homocitrate synthase. Magnaporthe species include, but are not limited to, *Magnaporthe rhizophila, Magnaporthe salvinii, Magnaporthe grisea* and *Magnaporthe poae* and the imperfect states of Magnaporthe in the genus Pyricularia. Preferably, the *Magnaporthe homocitrate* synthase is from *Magnaporthe grisea.*

In various embodiments, the homocitrate synthase can be from Powdery Scab (*Spongospora subterranea*); Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gacumannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Sclerotinia sclerotiorum*), and the like.

Fragments of a homocitrate synthase polypeptide may be used in the methods of the invention, preferably if the fragments include an intact or nearly intact epitope that occurs on the biologically active wildtype homocitrate synthase. The fragments comprise at least 10 consecutive amino acids of a homocitrate synthase. Preferably, the fragment comprises at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430 or at least 440 consecutive amino acids residues of a homocitrate synthase. In one embodiment, the fragment is from a Magnaporthe homocitrate synthase. Preferably, the fragment contains an amino acid sequence conserved among fungal homocitrate synthases.

Polypeptides having at least 50% sequence identity with a fungal homocitrate synthase are also useful in the methods of the invention. Preferably, the sequence identity is at least 60%, more preferably the sequence identity is at least 70%, most preferably the sequence identity is at least 80% or 90 or 95 or 99%, or any integer from 60–100% sequence identity in ascending order.

In addition, it is preferred that the polypeptide has at least 10% of the activity of a fungal homocitrate synthase. More preferably, the polypeptide has at least 25%, at least 50%, at least 75% or at least 90% of the activity of a fungal homocitrate synthase. Most preferably, the polypeptide has at least 10%, at least 25%, at least 50%, at least 75% or at least 90% of the activity of the *M. grisea* homocitrate synthase protein.

Thus, in another embodiment, the invention provides a method for identifying a test compound as a candidate for a fungicide, comprising:

a) contacting said test compound with at least one polypeptide selected from the group consisting of: a polypeptide having at least ten consecutive amino acids of a fungal homocitrate synthase, a polypeptide having at least 50% sequence identity with a fungal homocitrate synthase, and a polypeptide having at least 10% of the activity thereof, and b) detecting the presence and/or absence of binding between said test compound and said polypeptide;

wherein binding indicates that said test compound is a candidate for an antibiotic.

Any technique for detecting the binding of a ligand to its target may be used in the methods of the invention. For example, the ligand and target are combined in a buffer. Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with a homocitrate synthase protein or a fragment or variant thereof, the unbound protein is removed and the bound homocitrate synthase is detected. In a preferred embodiment, bound homocitrate synthase is detected using a labeled binding partner, such as a labeled antibody. In a variation of this assay, homocitrate synthase is labeled prior to contacting the immobilized candidate ligands. Preferred labels include fluorescent or radioactive moieties. Preferred detection methods include fluorescence correlation spectroscopy (FCS) and FCS-related confocal nanofluorimetric methods.

Once a compound is identified as a candidate for an antibiotic, it can be tested for the ability to inhibit homocitrate synthase enzymatic activity. The compounds can be tested using either in vitro or cell based assays. Alternatively, a compound can be tested by applying it directly to a fungus or fungal cell, or expressing it therein, and monitoring the fungus or fungal cell for changes or decreases in growth, development, viability, pathogenicity, or alterations in gene expression. Thus, in one embodiment, the invention provides a method for determining whether a compound identified as an antibiotic candidate by an above method has antifungal activity, further comprising: contacting a fungus or fungal cells with said antifungal candidate and detecting a decrease in the growth, viability, or pathogenicity of said fungus or fungal cells.

By decrease in growth, is meant that the antifungal candidate causes at least a 10% decrease in the growth of the fungus or fungal cells, as compared to the growth of the fungus or fungal cells in the absence of the antifungal candidate. By a decrease in viability is meant that at least 20% of the fungal cells, or portion of the fungus contacted with the antifungal candidate are nonviable. Preferably, the growth or viability will be decreased by at least 40%. More preferably, the growth or viability will be decreased by at least 50%, 75% or at least 90% or more. Methods for measuring fungal growth and cell viability are known to those skilled in the art. By decrease in pathogenicity, is meant that the antifungal candidate causes at least a 10% decrease in the disease caused by contact of the fungal pathogen with its host, as compared to the disease caused in the absence of the antifungal candidate. Preferably, the disease will be decreased by at least 40%. More preferably, the disease will be decreased by at least 50%, 75% or at least 90% or more. Methods for measuring fungal disease are well known to those skilled in the art, and include such metrics as lesion formation, lesion size, sporulation, respiratory failure, and/or death.

The ability of a compound to inhibit homocitrate synthase activity can be detected using in vitro enzymatic assays in which the disappearance of a substrate or the appearance of a product is directly or indirectly detected. Homocitrate synthase catalyzes the irreversible or reversible reaction acetyl-CoA and $H_2O$ and 2-oxoglutarate=2-hydroxybutane-1,2,4-tricarboxylate and CoA (see FIG. 1). Methods for detection of 2-hydroxybutane-1,2,4-tricarboxylate, CoA, acetyl-CoA, and/or 2-oxoglutarate, include spectrophotometry, mass spectroscopy, thin layer chromatography (TLC) and reverse phase HPLC.

Thus, the invention provides a method for identifying a test compound as a candidate for an antibiotic, comprising either:

a) contacting acetyl-CoA and $H_2O$ and 2-oxoglutarate with a homocitrate synthase;

b) contacting acetyl-CoA and $H_2O$ and 2-oxoglutarate with homocitrate synthase and said test compound; and c) determining the change in concentration for at least one of the following: 2-hydroxybutane-1,2,4-tricarboxylate, 2-oxoglutarate, acetyl-CoA, CoA, and/or $H_2O$.

wherein a change in concentration for any of the above substances indicates that said test compound is a candidate for an antibiotic or, a) contacting 2-hydroxybutane-1,2,4-tricarboxylate and CoA with a homocitrate synthase;

b) contacting 2-hydroxybutane-1,2,4-tricarboxylate and CoA with a homocitrate synthase and said test compound; and c) determining the change in concentration for at least one of the following: 2-hydroxybutane-1,2,4-tricarboxylate, 2-oxoglutarate, acetyl-CoA, CoA, and/or $H_2O$.

wherein a change in concentration for any of the above substances indicates that said test compound is a candidate for an antibiotic.

Enzymatically active fragments of a fungal homocitrate synthase are also useful in the methods of the invention. For example, a polypeptide comprising at least 100 consecutive amino acid residues of a fungal homocitrate synthase may be used in the methods of the invention. In addition, a polypeptide having at least 50%, 60%, 70%, 80%, 90%, 95% or at least 98% sequence identity with a fungal homocitrate synthase may be used in the methods of the invention. Most preferably, the polypeptide has at least 50% sequence identity with a fungal homocitrate synthase and at least 10%, 25%, 75% or at least 90% of the activity thereof.

Thus, the invention provides a method for identifying a test compound as a candidate for a fungicide, comprising:

a) contacting acetyl-CoA and $H_2O$ and 2-oxoglutarate with a polypeptide selected from the group consisting of: a polypeptide having at least 50% sequence identity with a homocitrate synthase, a polypeptide having at least 50% sequence identity with a homocitrate synthase and having at least 10% of the activity thereof, and a polypeptide comprising at least 100 consecutive amino acids of a homocitrate synthase b) contacting acetyl-CoA and $H_2O$ and 2-oxoglutarate with said polypeptide and said test compound; and c) determining the change in concentration for at least one of the following: 2-hydroxybutane-1,2,4-tricarboxylate, 2-oxoglutarate, acetyl-CoA, CoA, and/or $H_2O$.

wherein a change in concentration for any of the above substances indicates that said test compound is a candidate for an antibiotic or, a) contacting 2-hydroxybutane-1,2,4-tricarboxylate and CoA with a polypeptide selected from the group consisting of: a polypeptide having at least 50% sequence identity with a homocitrate synthase, a polypeptide having at least 50% sequence identity with a homocitrate synthase and at least 10% of the activity thereof, and a polypeptide comprising at least 100 consecutive amino acids of a homocitrate synthase b) contacting 2-hydroxybutane-1,2,4-tricarboxylate and CoA, with said polypeptide and said test compound; and c) determining the change in concentration for at least one of the following, 2-hydroxybutane-1,2,4-tricarboxylate, 2-oxoglutarate, acetyl-CoA, CoA, and/or $H_2O$.

wherein a change in concentration for any of the above substances indicates that said test compound is a candidate for an antibiotic.

For the in vitro enzymatic assays, homocitrate synthase protein and derivatives thereof may be purified from a fungus or may be recombinantly produced in and purified from an archael, bacterial, fungal, or other eukaryotic cell culture. Preferably these proteins are produced using an *E. coli*, yeast, or filamentous fungal expression system. Methods for the purification of homocitrate synthase may be described in Jaklitsch and Kubicek (Jaklitsch, W. M. and C. P. Kubicek (1990) Biochem J 269: 247–53 (PMID: 2115771)). Other methods for the purification of homocitrate synthase proteins and polypeptides are known to those skilled in the art.

As an alternative to in vitro assays, the invention also provides cell based assays. In one embodiment, the invention provides a method for identifying a test compound as a candidate for a antibiotic, comprising:

a) measuring the expression of a homocitrate synthase in a cell, cells, tissue, or an organism in the absence of said compound;

b) contacting said cell, cells, tissue, or organism with said test compound and measuring the expression of said homocitrate synthase in said cell, cells, tissue, or organism;

c) comparing the expression of homocitrate synthase in steps (a) and (b);

wherein a lower expression in the presence of said test compound indicates that said compound is a candidate for an antibiotic.

Expression of homocitrate synthase can be measured by detecting the HCS1 primary transcript or mRNA, homocitrate synthase polypeptide, or homocitrate synthase enzymatic activity. Methods for detecting the expression of RNA and proteins are known to those skilled in the art. See, for example, *Current Protocols in Molecular Biology* Ausubel et al., eds., Greene Publishing and Wiley-Interscience, New York, 1995. The method of detection is not critical to the invention. Methods for detecting HCS1 RNA include, but are not limited to amplification assays such as quantitative reverse transcriptase-PCR, and/or hybridization assays such as Northern analysis, dot blots, slot blots, in-situ hybridization, transcriptional fusions using a HCS1 promoter fused to a reporter gene, DNA assays, and microarray assays.

Methods for detecting protein expression include, but are not limited to, immunodetection methods such as Western blots, ELISA assays, polyacrylamide gel electrophoresis, mass spectroscopy, and enzymatic assays. Also, any reporter gene system may be used to detect HCS1 protein expression. For detection using gene reporter systems, a polynucleotide encoding a reporter protein is fused in frame with HCS1, so as to produce a chimeric polypeptide. Methods for using reporter systems are known to those skilled in the art.

Chemicals, compounds or compositions identified by the above methods as modulators, preferably inhibitors, of HCS1 expression or activity can then be used to control fungal growth. Diseases such as rusts, mildews, and blights spread rapidly once established. Fungicides are thus routinely applied to growing and stored crops as a preventive measure, generally as foliar sprays or seed dressings. For example, compounds that inhibit fungal growth can be applied to a fungus or expressed in a fungus, in order to prevent fungal growth. Thus, the invention provides a method for inhibiting fungal growth, comprising contacting a fungus with a compound identified by the methods of the invention as having antifungal activity.

Antifungals and antifungal inhibitor candidates identified by the methods of the invention can be used to control the growth of undesired fungi, including ascomycota, zygomycota, basidiomycota, chytridiomycota, and lichens.

Examples of undesired fungi include, but are not limited to Powdery Scab (*Spongospora subterranea*), Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gaeunmannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Scierotinia sclerotiorum*), diseases of animals such as infections of lungs, blood, brain, skin, scalp, nails or other tissues (*Aspergillus fumigatus* Aspergillus sp. Fusraium sp., Trichophyton sp., Epidermophyton sp., and Microsporum sp., and the like).

Also provided is a method of screening for an antibiotic by determining whether a test compound is active against the gene identified (SEQ ID NO: 1 or SEQ ID NO: 2), its gene product (SEQ ID NO: 3), or the biochemical pathway or pathways it functions on.

In one particular embodiment, the method is performed by providing an organism having a first form of the gene corresponding to either SEQ ID NO: 1 or SEQ ID NO: 2, either a normal form, a mutant form, a homologue, or a heterologous HCS1 gene that performs a similar function as HCS1. The first form of HCS1 may or may not confer a growth conditional phenotype, i.e., a lysine requiring phenotype, and/or a hypersensitivity or hyposensitivity phenotype on the organism having that altered form. In one particular embodiment a mutant form contains a transposon insertion. A comparison organism having a second form of an HCS1, different from the first form of the gene is also provided, and the two organisms are separately contacted with a test compound. The growth of the two organisms in the presence of the test compound is then compared.

Thus, in one embodiment, the invention provides a method for identifying a test compound as a candidate for an antibiotic, comprising:

a) providing cells having one form of a homocitrate synthase gene, and providing comparison cells having a different form of a homocitrate synthase gene, b) contacting said cells and said comparison cells with a test compound and determining the growth of said cells and comparison cells in the presence of the test compound, wherein a difference in growth between said cells and said comparison cells in the presence of said test compound indicates that said test compound is a candidate for an antibiotic.

It is recognized in the art that the optional determination of the growth of said first organism and said comparison second organism in the absence of any test compounds may be performed to control for any inherent differences in growth as a result of the different genes. It is also recognized that any combination of two different forms of an HCS1 gene, including normal genes, mutant genes, homologues, and functional homologues may be used in this method. Growth and/or proliferation of an organism is measured by methods well known in the art such as optical density measurements, and the like. In a preferred embodiment the organism is *Magnaporthe grisea.*

Conditional lethal mutants may identify particular biochemical and/or genetic pathways given that at least one identified target gene is present in that pathway. Knowledge of these pathways allows for the screening of test compounds as candidates for antibiotics as inhibitors of the substrates, products and enzymes of the pathway. Pathways known in the art may be found at the Kyoto Encyclopedia of Genes and Genomes and in standard biochemistry texts (Lehninger, A., D. Nelson, et al. (1993) *Principles of Biochemistry*. New York, Worth Publishers).

Thus, in one embodiment, the invention provides a method for screening for test compounds acting against the biochemical and/or genetic pathway or pathways in which HCS1 functions, comprising:

a) providing cells having one form of a gene in the lysine biochemical and/or genetic pathway and providing comparison cells having a different form of said gene.

b) contacting said cells and comparison cells with a said test compound, c) determining the growth of said cells and comparison cells in the presence of said test compound.

wherein a difference in growth between said cells and said comparison cells in the presence of said compound indicates that said compound is a candidate for an antibiotic.

The use of multi-well plates for screening is a format that readily accommodates multiple different assays to characterize various compounds, concentrations of compounds, and fungal strains in varying combinations and formats. Certain testing parameters for the screening method can significantly affect the identification of growth inhibitors, and thus can be manipulated to optimize screening efficiency and/or reliability. Notable among these factors are variable sensitivities of different mutants, increasing hypersensitivity with increasingly less permissive conditions, an apparent increase in hypersensitivity with increasing compound concentration, and other factors known to those in the art.

Conditional lethal mutants may identify particular biochemical and/or genetic pathways given that at least one identified target gene is present in that pathway. Knowledge of these pathways allows for the screening of test compounds as candidates for antibiotics. Pathways known in the art may be found at the Kyoto Encyclopedia of Genes and Genomes and in standard biochemistry texts (Lehninger, A., D. Nelson, et al. (1993) *Principles of Biochemistry*. New York, Worth Publishers). Thus, in one embodiment, the invention provides a method for screening for test compounds acting against the biochemical and/or genetic pathway or pathways in which HCS1 functions, comprising:

(a) providing paired growth media; comprising a first medium and a second medium, wherein said second medium contains a higher level of lysine than said first medium;

(b) contacting an organism with said test compound;

(c) inoculating said first and second media with said organism; and (d) determining the growth of said organism;

wherein a difference in growth of the organism between said first and second media indicates that said test compound is a candidate for an antibiotic.

It is recognized in the art that the optional determination of the growth of said organism in the paired media in the absence of any test compounds may be performed to control for any inherent differences in growth as a result of the different media. Growth and/or proliferation of an organism is measured by methods well known in the art such as optical density measurements, and the like. In a preferred embodiment, the organism is *Magnaporthe grisea.*

EXPERIMENTAL

Example 1

Construction of Plasmids With a Transposon Containing a Selectable Marker

Construction of Sif transposon: Sif was constructed using the GPS3 vector from the GPS-M mutagenesis system from New England Biolabs, Inc. (Beverly, Mass.) as a backbone. This system is based on the bacterial transposon Tn7. The following manipulations were done to GPS3 according to Sambrook et al. (1989) *Molecular Cloning, a Laboratory Manual*, Cold Spring Harbor Laboratory Press. The kanamycin resistance gene (npt) contained between the Tn7 arms was removed by EcoRV digestion. The bacterial hygromycin B phosphotransferase (hph) gene (Gritz and Davies (1983) Gene 25: 179–88 (PMID: 6319235)) under control of the *Aspergillus nidulans* trpC promoter and terminator (Mullaney et al. (1985) Mol Gen Genet 199: 37–45 (PMID: 3158796)) was cloned by a HpaI/EcoRV blunt ligation into the Tn7 arms of the GPS3 vector yielding pSif1. Excision of the ampicillin resistance gene (bla) from pSif1 was achieved by cutting pSif1 with XmnI and BglI followed by a T4 DNA polymerase treatment to remove the 3' overhangs left by the BglI digestion and religation of the plasmid to yield pSif. Top 10F' electrocompetent *E. coli* cells (Invitrogen) were transformed with ligation mixture according to manufacturer's recommendations. Transformants containing the Sif transposon were selected on LB agar (Sambrook et al. (1989) *Molecular Cloning, a Laboratory Manual*, Cold Spring Harbor Laboratory Press.) containing 50 ug/ml of hygromycin B (Sigma Chem. Co., St. Louis, Mo.).

Example 2

Construction of a Cosmid Library Containing Fungal Genes and a Selectable Marker Cosmid libraries were constructed in the pcosKA5 vector (Hamer et al. (2001) Proc Natl Acad Sci USA 98: 5110–15 (PMID: 11296265)) as described in Sambrook et al. (1989) *Molecular Cloning a Laboratory Manual*, Cold Spring Harbor Laboratory Press. Cosmid libraries were quality checked by pulsed-field gel electrophoresis, restriction digestion analysis, and PCR identification of single genes.

Example 3

Construction of Cosmids With Transposon Inserted into Fungal Genes

Sif Transposition into a Cosmid: Transposition of Sif into the cosmid framework was carried out as described by the GPS-M mutagenesis system (New England Biolabs, Inc.). Briefly, 2 ul of the 10× GPS buffer, 70 ng of supercoiled pSIF, 8–12 μg of target cosmid DNA were mixed and taken to a final volume of 20 ul with water. 1 ul of transposase (TnsABC) was added to the reaction and incubated for 10 minutes at 37° C. to allow the assembly reaction to happen. After the assembly reaction 1 ul of start solution was added to the tube, mixed well and incubated for 1 hour at 37° C. followed by heat inactivation of the proteins at 75° C. for 10 min. Destruction of the remaining untransposed pSif was done by PISceI digestion at 37° C. for 2 hours followed by 10 min incubation at 75° C. to inactivate the proteins. Transformation of Top10F' electrocompetent cells (Invitrogen) was done according to manufacturers recommendations. Sif-containing cosmid transformants were selected by growth on LB agar plates containing 50 ug/ml of hygromycin B (Sigma Chem. Co.) and 100 ug/ml of Ampicillin (Sigma Chem. Co.).

Example 4

High Throughput Preparation and Verification of Insertion of Transposon into Fungal Genes

*E. coli* strains containing cosmids with transposon insertions were picked to 96 well growth blocks (Beckman Co.) containing 1.5 ml of TB (Terrific Broth, Sambrook et al. (1989) *Molecular Cloning, a Laboratory Manual*, Cold Spring Harbor Laboratory Press) supplemented with 50 ug/ml of ampicillin. Blocks were incubated with shaking at 37 C overnight. *E. coli* cells were pelleted by centrifugation and cosmids were isolated by a modified alkaline lysis method (Marra et al. (1997) Genome Res 7: 1072–84 (PMID: 9371743)). DNA quality was checked by electrophoresis on agarose gels. Cosmids were sequenced using primers from the ends of each transposon and commercial dideoxy sequencing kits (Big Dye Terminators, Perkin Elmer Co.). Sequencing reactions were analyzed on an ABI377 DNA sequencer (Perkin Elmer Co.).

DNA sequences adjacent to the site of the insertion were collected and used to search DNA and protein databases using the BLAST algorithms (Altschul et al. (1997) Nucleic Acids Res 25: 3389–3402 (PMID: 9254694)). A single insertion of SIF into the *Magnaporthe grisea* HCS1 gene was chosen for further analysis. This construct was designated cpgmra0023008h04 and it contains the SIF transposon between amino acids 334 and 335 relative to the *Penicillium chrysogenum* homologue (total length—474 amino acids, GENBANK: PCAJ3630 accession number AJ223630).

Example 5

Preparation of Cosmid DNA and Transformation of the Fungus *Magnaporthe grisea*

Cosmid DNA from the HCS1 transposon tagged cosmid clone was prepared using QIAGEN Plasmid Maxi Kit (QIAGEN), and digested by PI-PspI (New England Biolabs, Inc.). Fungal electro-transformation was performed essentially as described (Wu et al. (1997) MPMI 10: 700–708). Briefly, *M. grisea* strain Guy 11 was grown in complete liquid media (Talbot et al. (1993) Plant Cell 5: 1575–1590 (PMID: 8312740)) shaking at 120 rpm for 3 days at 25° C. in the dark. Mycelia was harvested and washed with sterile $H_2O$ and digested with 4 mg/ml beta-glucanase (InterSpex) for 4–6 hours to generate protoplasts. Protoplasts were collected by centrifugation and resuspended in 20% sucrose at the concentration of $2\times10^8$ protoplasts/ml. 50 ul protoplast suspension was mixed with 10–20 ug of the cosmid DNA and pulsed using Gene Pulser II (BioRad) set with the following parameters: resistance 200 ohm, capacitance 25 uF, voltage 0.6 kV. Transformed protoplasts were regenerated in complete agar media (C M, Talbot et al. (1993) Plant Cell 5: 1575–1590 (PMID: 8312740)) with the addition of 20% sucrose for one day, then overlayed with CM agar media containing hygromycin B (250 ug/ml) to select transformants. Transformants were screened for homologous recombination events in the target gene by PCR (Hamer et al. (2001) Proc Natl Acad Sci USA 98: 5110–15 (PMID: 11296265)). Two independent strains were identified and are hereby referred to as KO1-1 and KO1-2, respectively.

Example 6

Effect of Transposon Insertion on Magnaporthe Pathogenicity

Figure 2:
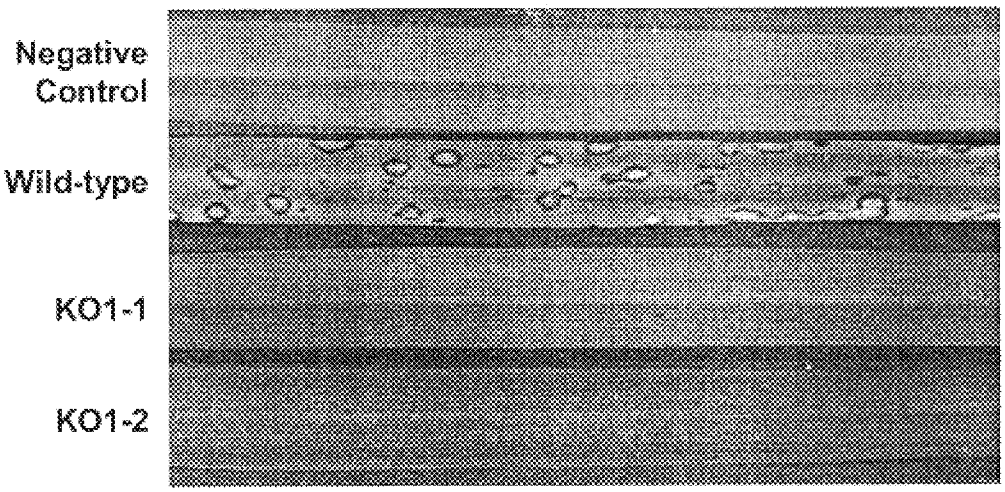
FIG. 2 shows a digital image showing the effect of HCS1 gene disruption on *Magnaporthe grisea* pathogenicity using whole plant infection assays. Rice variety CO39 was inoculated with wild-type and the transposon insertion strains, KO1-1 and KO1-2. Leaf segments were imaged at five days post-inoculation.

The target fungal strains, KO1-1 and KO1-2, obtained in Example 5 and the wild type strain, Guy11, were subjected to a pathogenicity assay to observe infection over a 1-week period. Rice infection assays were performed using Indian rice cultivar CO39 essentially as described in Valent et al. ((1991) Genetics 127: 87–101 (PMID: 2016048)). All three strains were grown for spore production on complete agar media. Spores were harvested and the concentration of spores adjusted for whole plant inoculations. Two-week-old seedlings of cultivar CO39 were sprayed with 12 ml of conidial suspension ($5\times10^4$ conidia per ml in 0.01% Tween-20 (Polyoxyethylensorbitan monolaureate) solution). The inoculated plants were incubated in a dew chamber at 27° C. in the dark for 36 hours, and transferred to a growth chamber (27° C. 12 hours/21° C. 12 hours 70% humidity) for an additional 5.5 days. Leaf samples were taken at 3, 5, and 7 days post-inoculation and examined for signs of successful infection (i.e. lesions). FIG. 2 shows the effects of HCS1 gene disruption on Magnaporthe infection at five days post-inoculation.

Example 7

Verification of Gene Function by Analysis of Nutritional Requirements

Figure 3A:
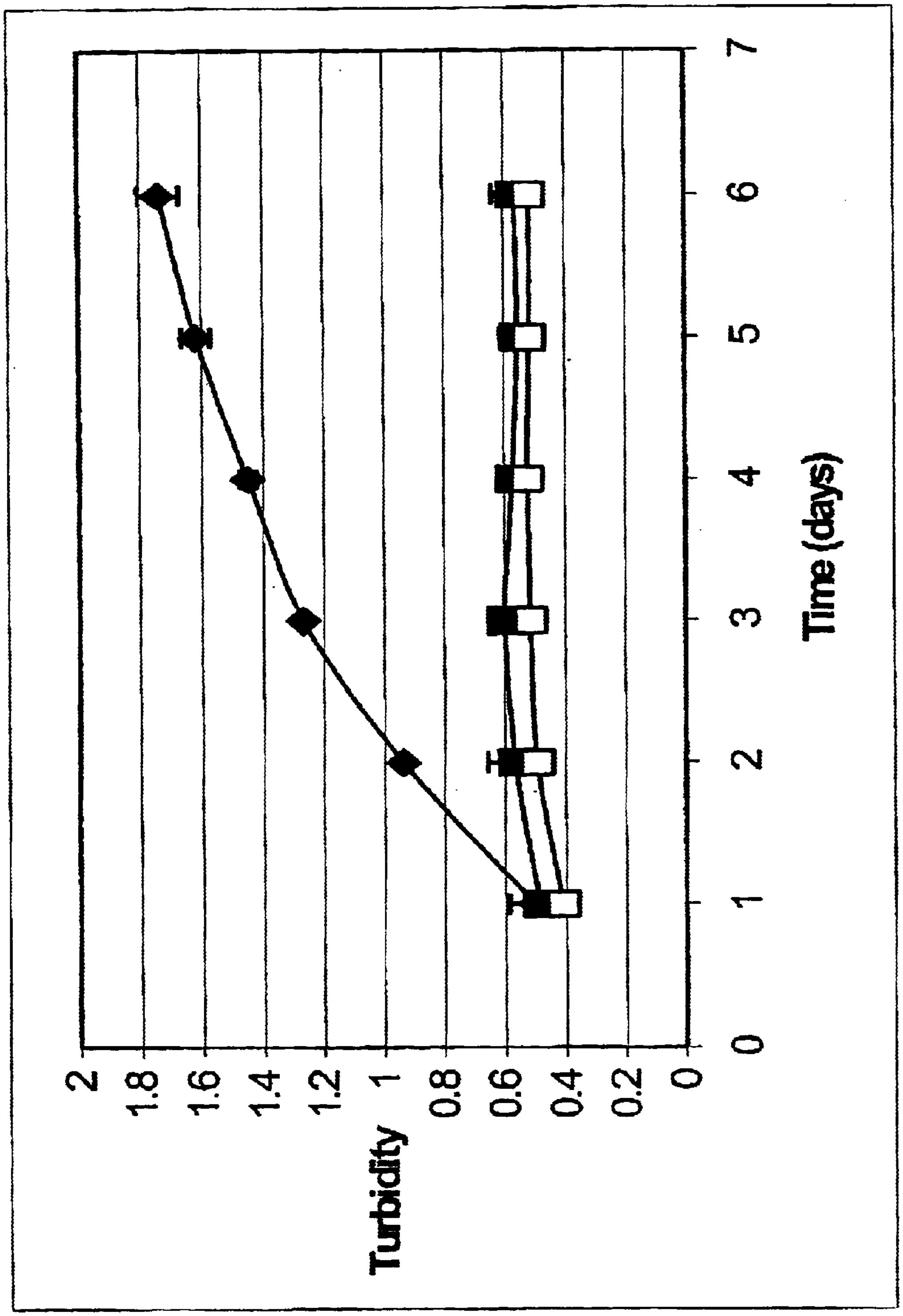
FIG. 3. Verification of Gene Function by Analysis of Nutritional Requirements. Wild-type and transposon insertion strains, KO1-1 and KO1-2, were grown in (A) minimal media and (B) minimal media with the addition of L-lysine, respectively. The x-axis shows time in days and the y-axis shows turbidity measured at 490 nanometers and 750 nanometers. The symbols represent wildtype (--♦--), transposon strain KO1-1 (--■--), and transposon strain KO1-2 (--▲--).
Figure 3B:
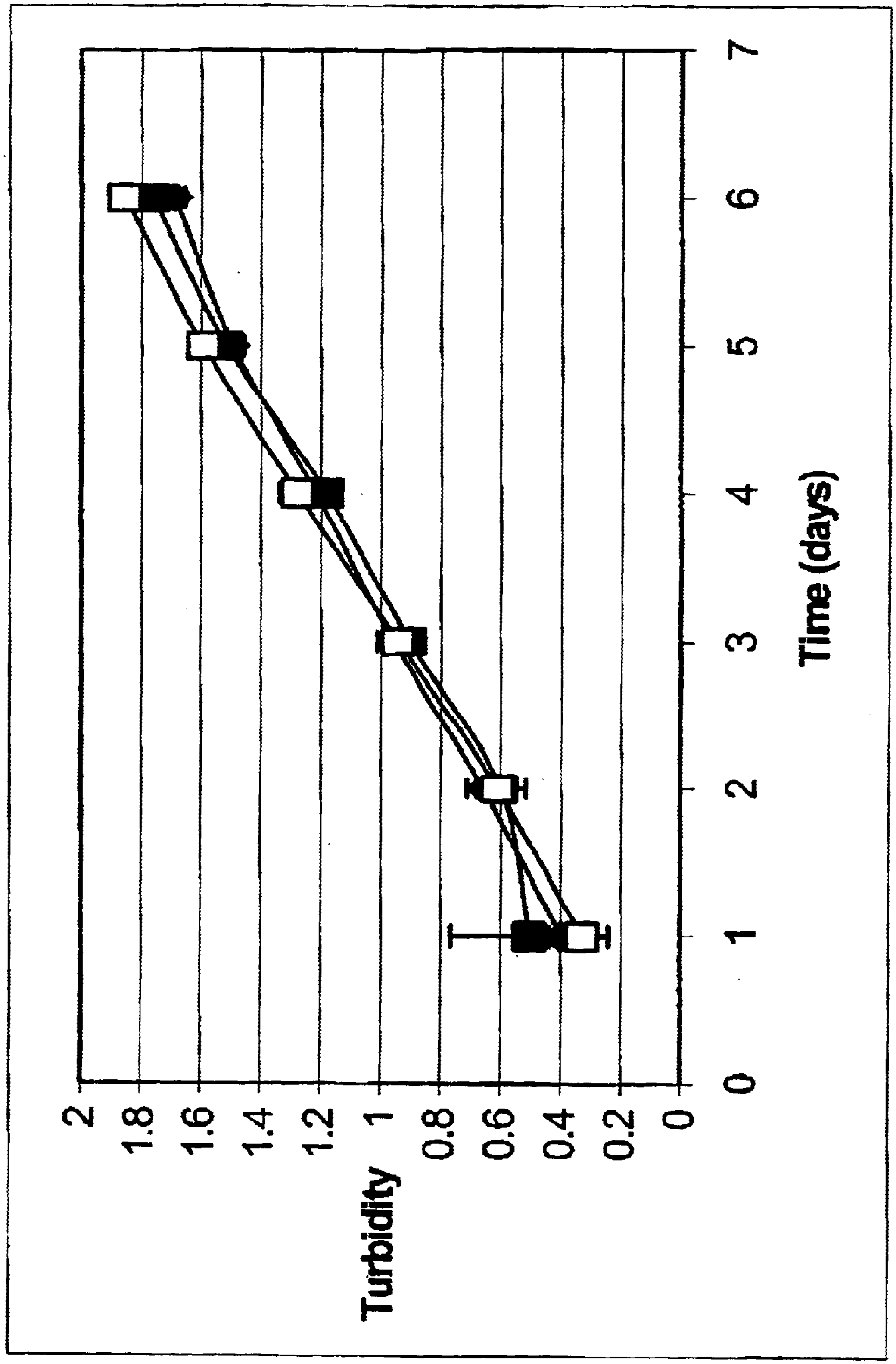

The fungal strains, KO1-1 and KO1-2, containing the HCS1 disrupted gene obtained in Example 5 were analyzed for their nutritional requirement for lysine using the PM5 phenotype microarray from Biolog, Inc. (Hayward, Calif.). The PM5 plate tests for the auxotrophic requirement for 94 different metabolites. The inoculating fluid consists of 0.05% Phytagel, 0.03% Pluronic F68, 1% glucose, 23.5 mM $NaNO_3$, 6.7 mM KCl, 3.5 mM $Na_2SO_4$, 11 mM $KH_2PO_4$, 0.01%p-iodonitrotetrazolium violet, 0.1 mM $MgCl_2$, 1.0 mM $CaCl_2$ and trace elements. Final concentrations of trace elements are: 7.6 μM $ZnCl_2$, 2.5 μM $MnCl_2.4H_2O$, 1.8 μM $FeCl_2.4H_2O$, 0.71 μM $CoCl_26H2O$, 0.64 μM $CuCl_22H_2O$, 0.62 μM $Na_2MoO_4$, 18 μM $H_3BO_3$. pH adjusted to 6.0 with NaOH. Spores for each strain were harvested into the inoculating fluid. The spore concentrations were adjusted to $2\times10^5$ spores/ml. 100 μl of spore suspension were deposited into each well of the microtiter plates. The plates were incubated at 25° C. for 7 days. Optical density (OD) measurements at 490 nm and 750 nm were taken daily. The $OD_{490}$ measures the extent of tetrazolium dye reduction and the level of growth, and $OD_{750}$ measures growth only. Turbidity=$OD_{490}$+$OD_{750}$. Data confirming the annotated gene function is presented as a graph of Turbidity vs. Time showing both the mutant fungi and the wild-type control in the absence (FIG. 3A) and presence (FIG. 3B) of L-lysine.

Example 8

Cloning and Expression Strategies, Extraction and Purification of the Homocitrate Synthase Protein The following protocol may be employed to obtain the purified the homocitrate synthase protein.

Cloning and Expression Strategies:

A HCS1 cDNA gene can be cloned into *E. coli* (pET vectors-Novagen), Baculovirus (Pharmingen) and Yeast (Invitrogen) expression vectors containing His/fusion protein tags. Evaluate the expression of recombinant protein by SDS-PAGE and Western blot analysis.

Extraction:

Extract recombinant protein from 250 ml cell pellet in 3 ml of extraction buffer By sonicating 6 times, with 6 sec pulses at 4° C. Centrifuge extract at 15000×g for 10 min and collect supernatant. Assess biological activity of the recombinant protein by activity assay.

Purification:

Purify recombinant protein by Ni-NTA affinity chromatography (Qiagen). Purification protocol: perform all steps at 4° C.:

Use 3 ml Ni-beads (Qiagen)

Equilibrate column with the buffer

Load protein extract

Wash with the equilibration buffer

Elute bound protein with 0.5 M imidazole

Example 9

Assays for Testing Binding of Test Compounds to Homocitrate Synthase

The following protocol may be employed to identify test compounds that bind to the homocitrate synthase protein.

Purified full length homocitrate synthase polypeptide with a His/fusion protein tag (Example 8) is bound to a HisGrab™ Nickel Coated Plate (Pierce, Rockford, Ill.) following manufacturer's instructions.

Buffer conditions are optimized (e.g. ionic strength or pH, Jaklitsch, W. M. and C. P. Kubicek (1990) Biochem J 269: 247–53 (PMID: 2115771)) for binding of radiolabeled (acetyl-1-$^{14}$C)-coenzyme A (Sigma-Aldrich Co.) to the bound HCS1.

Screening of test compounds is performed by adding test compound and (acetyl-1-$^{14}$C)-coenzyme A (Sigma-Aldrich Co.) to the wells of the HisGrab™ plate containing bound HCS1.

The wells are washed to remove excess labeled ligand and scintillation fluid (Scintiverse®, Fisher Scientific) is added to each well.

The plates are read in a microplate scintillation counter.

Candidate compounds are identified as wells with lower radioactivity as compared to control wells with no test compound added.

Additionally, a purified polypeptide comprising 10–50 amino acids from the *M. grisea* homocitrate synthase is screened in the same way. A polypeptide comprising 10–50 amino acids is generated by subcloning a portion of the HCS1 gene into a protein expression vector that adds a His-Tag when expressed (see Example 8). Oligonucleotide primers are designed to amplify a portion of the HCS1 gene using the polymerase chain reaction amplification method. The DNA fragment encoding a polypeptide of 10–50 amino acids is cloned into an expression vector, expressed in a host organism and purified as described in Example 8 above.

Test compounds that bind HCS1 are further tested for antibiotic activity. *M. grisea* is grown as described for spore production on oatmeal agar media (Talbot et al. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 μg/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 10

Assays for Testing Inhibitors or Candidates for Inhibition of Homocitrate Synthase Activity The enzymatic activity of homocitrate synthase is determined in the presence and absence of candidate compounds in a suitable reaction mixture, such as described by Gray and Bhattacharjee (Gray, G S and Bhattacharjee, J K (1976) Can J Microbiol 22: 1664–7 (PMID: 10066)), or Jaklitsch, W. M. and C. P. Kubicek (1990) Biochem J 269: 247–53 (PMID: 2115771). Candidate compounds are identified when a decrease in products or a lack of decrease in substrates is detected with the reaction proceeding in either direction.

Additionally, the enzymatic activity of a polypeptide comprising 10–50 amino acids from the *M. grisea* homocitrate synthase is determined in the presence and absence of candidate compounds in a suitable reaction mixture, such as described by Gray and Bhattacharjee (Gray, G S and Bhattacharjee, J K (1976) Can J Microbiol 22: 1664–7 (PMID: 10066)), or Jaklitsch, W. M. and C. P. Kubicek (1990) Biochem J 269: 247–53 (PMID: 2115771). A polypeptide comprising 10–50 amino acids is generated by subcloning a portion of the HCS1 gene into a protein expression vector that adds a His-Tag when expressed (see Example 8). Oligonucleotide primers are designed to amplify a portion of the HCS1 gene using polymerase chain reaction amplification method. The DNA fragment encoding a polypeptide of 10–50 amino acids is cloned into an expression vector, expressed and purified as described in Example 8 above.

Test compounds identified as inhibitors of HCS1 activity are further tested for antibiotic activity. *Magnaporthe grisea* fungal cells are grown under standard fungal growth conditions that are well known and described in the art. *M. grisea* is grown as described for spore production on oatmeal agar media (Talbot et al. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 $\mu$g/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 11

Assays for Testing Compounds or Candidates for Compounds That Alter the Expression of the Homocitrate Synthase Gene

*Magnaporthe grisea* fungal cells are grown under standard fungal growth conditions that are well known and described in the art. Wild-type *M. grisea* spores are harvested from cultures grown on complete agar or oatmeal agar media after growth for 10–13 days in the light at 25° C. using a moistened cotton swab. The concentration of spores is determined using a hemacytometer and spore suspensions are prepared in a minimal growth medium to a concentration of $2\times10^5$ spores per ml. 25 ml cultures are prepared to which test compounds will be added at various concentrations. A culture with no test compound present is included as a control. The cultures are incubated at 25° C. for 3 days after which test compound or solvent only control is added. The cultures are incubated an additional 18 hours. Fungal mycelia is harvested by filtration through Miracloth (CalBiochem®, La Jolla, Calif.), washed with water and frozen in liquid nitrogen. Total RNA is extracted with TRIZOL® Reagent using the methods provided by the manufacturer (Life Technologies, Rockville, Md.). Expression is analyzed by Northern analysis of the RNA samples as described (Sambrook et al. (1989) *Molecular Cloning, a Laboratory Manual*, Cold Spring Harbor Laboratory Press) using a radiolabeled fragment of the HCS1 gene as a probe. Test compounds resulting in a reduced level of HCS1 mRNA relative to the untreated control sample are identified as candidate antibiotic compounds.

Example 12

In Vivo Cell Based Assay Screening Protocol With a Fungal Strain Containing a Mutant Form of Homocitrate Synthase With No Activity

*Magnaporthe grisea* fungal cells containing a mutant form of the HCS1 gene which abolishes enzyme activity, such as a gene containing a transposon insertion (see Examples 4 and 5), are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium containing 100 $\mu$M L-lysine to a concentration of $2\times10^5$ spores per ml. Approximately $4\times10^4$ spores are added to each well of 96-well plates to which a test compound is added (at varying concentrations). The total volume in each well is 200 $\mu$l. Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 13

In Vivo Cell Based Assay Screening Protocol With a Fungal Strain Containing a Mutant Form of Homocitrate Synthase With Reduced Activity

*Magnaporthe grisea* fungal cells containing a mutant form of the HCS1 gene, such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores are added to each well of 96-well plates to which a test compound is added (at varying concentrations). The total volume in each well is 200 $\mu$l.

Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild-type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 14

In Vivo Cell Based Assay Screening Protocol With a Fungal Strain Containing a Mutant Form of a Lysine Biosynthetic Gene With No Activity

*Magnaporthe grisea* fungal cells containing a mutant form of a gene in the lysine biosynthetic pathway (e.g. L-Aminoadipate-semialdehyde dehydrogenase (E. C. 1.2.1.31)) are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium containing 100 μM L-lysine to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 μl. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild-type are identified as potential antifungal compounds. Similar protocols may be found in Kirsch and DiDomenico ((1994) Biotechnology 26: 177–221 (PMID: 7749303)).

Example 15

In Vivo Cell Based Assay Screening Protocol With a Fungal Strain Containing a Mutant Form of a Lysine Biosynthetic Gene With Reduced Activity

*Magnaporthe grisea* fungal cells containing a mutant form of a gene in the lysine biosynthetic pathway (e.g. L-Aminoadipate-semialdehyde dehydrogenase (E. C. 1.2.1.31)), such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* fungal cells containing a mutant form of are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 μl. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 16

In Vivo Cell Based Assay Screening Protocol With a Fungal Strain Containing a Fungal HCS1 and a Second Fungal Strain Containing a Heterologous HCS1 Gene Wild-type *Magnaporthe grisea* fungal cells and *M. grisea* fungal cells lacking a functional HCS1 gene and containing a HCS1 gene from *Thermus aquaticus* (Genbank accession 087198, 56% sequence identity) are grown under standard fungal growth conditions that are well known and described in the art. A *M. grisea* strain carrying a heterologous HCS1 gene is made as follows:

A *M. grisea* strain is made with a nonfunctional HCS1 gene, such as one containing a transposon insertion in the native gene (see Examples 4 and 5).

A construct containing a heterologous HCS1 gene is made by cloning the HCS1 gene from *Thermus aquaticus* into a fungal expression vector containing a trpC promoter and terminator (e.g. pCB1003, Carroll et al. (1994) Fungal Gen News Lett 41: 22) using standard molecular biology techniques that are well known and described in the art (Sambrook et al. (1989) *Molecular Cloning, a Laboratory Manual*, Cold Spring Harbor Laboratory Press).

The said construct is used to transform the *M. grisea* strain lacking a functional HCS1 gene (see Example 5). Transformants are selected on minimal agar medium lacking L-lysine. Only transformants carrying a functional HCS1 gene will grow.

Wild-type strains of *Magnaporthe grisea* and strains containing a heterologous form of HCS1 are grown under standard fungal growth conditions that are well known and described in the art. *Magnaporthe grisea* spores are harvested from cultures grown on complete agar medium after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 μl. Wells with no test compound present, and wells without cells are included as controls. The plates are incubated at 25° C. for seven days and optical density measurements at 590 nm are taken daily. The effect of each compound on the wild-type and heterologous fungal strains is measured against the growth control and the percent of inhibition is calculated as the $OD_{590}$ (fungal strain plus test compound)/$OD_{590}$ (growth control)×100. The percent of growth inhibition as a result of a test compound on the wild-type and heterologous fungal strains are compared. Compounds that show differential growth inhibition between the wild-type and heterologous strains are identified as potential antifungal compounds with specificity to the native or heterologous HCS1 gene products. Similar protocols may be found in Kirsch and DiDomenico ((1994) Biotechnology 26: 177–221 (PMID: 7749303)).

Example 17

Pathway Specific In Vivo Assay Screening Protocol

*Magnaporthe grisea* fungal cells are grown under standard fungal growth conditions that are well known and described in the art. Wild-type *M. grisea* spores are harvested from cultures grown on oatmeal agar media after growth for 10–13 days in the light at 25° C. using a moistened cotton swab. The concentration of spores is determined using a hemocytometer and spore suspensions are prepared in a minimal growth medium and a minimal growth medium containing 4 mM L-lysine (Sigma-Aldrich Co.) to a concentration of $2\times10^5$ spores per ml. The minimal growth media contains carbon, nitrogen, phosphate, and sulfate sources, and magnesium, calcium, and trace elements (for example, see inoculating fluid in Example 7). Spore suspensions are added to each well of a 96-well microtiter plate (approximately $4\times10^4$ spores/well). For each well containing a spore suspension in minimal media, an additional well is present containing a spore suspension in minimal medium containing 4 mM L-lysine. Test compounds are added to wells containing spores in minimal media and minimal media containing L-lysine. The total volume in each well is 200 μl. Both minimal media and L-lysine containing media wells with no test compound are provided as controls. The plates are incubated at 25° C. for seven days and optical density measurements at 590 nm are taken daily. A compound is identified as a candidate for an antibiotic acting against the lysine biosynthetic pathway when the observed growth in the well containing minimal media is less than the observed growth in the well containing L-lysine as a result of the addition of the test compound. Similar protocols may be found in Kirsch and DiDomenico ((1994) Biotechnology 26: 177–221 (PMID: 7749303)).

While the foregoing describes certain embodiments of the invention, it will be understood by those skilled in the art that variations and modifications may be made and still fall within the scope of the invention. The foregoing examples are intended to exemplify various specific embodiments of the invention and do not limit its scope in any manner.

What is claimed is:

1. A method for identifying a test compound as a candidate for an antibiotic, comprising:

a) contacting a homocitrate synthase polypeptide with a test compound, wherein the homocitrate synthase polypeptide is selected from the group consisting of *Spongospora subterrane, Botrytis cinerea, Armillaria mellea, Ganoderma adspersum, Piptoporus betulinus, Ustilago maydis, Polyporus squamosus, Cercospora zeae-maydis, Armillaria gallica, Armillaria luteobubalina, Armillaria ostoyae, Colletotrichum musae, Monilinia fructigena, Penicillium expansum, Plasmodiophora brassicae, Phytophthora infestans, Heterobasidion annosum, Gaeumannomyces graminis, Ophiostoma ulmi, Uromyces appendiculatus, Cochliobolus carbonum, Periconia circinata, Cochliobolus heterostrophus, Cochliobolus lunata, Cochliobolus stenospilus, Fusarium oxysporum, Fusarium graminearum, Fusarium culmorum, Rhizoctonia solani, Puccinia graminis, Sclerotinia sclerotiorum, Magnaporthe rhizophila, Magnaporthe salvinii, Magnaporthe grisea, Magnaporthe poae* and *Magnaporthe Pyricularia*; and b) detecting the presence or absence of binding between said test compound and said homocitrate synthase polypeptide;

wherein binding indicates that said test compound is a candidate for an antibiotic.

2. The method of claim 1, wherein said homocitrate synthase polypeptide is a Magnaporthe homocitrate synthase polypeptide.

3. The method of claim 1, wherein said homocitrate synthase polypeptide is SEQ ID NO: 3.

4. A method for identifying a test compound as a candidate for an antibiotic, comprising:

a) contacting acetyl-CoA and $H_2O$ and 2-oxoglutarate with a homocitrate synthase;

b) contacting acetyl-CoA and $H_2O$ and 2-oxoglutarate with a homocitrate synthase and said test compound; and c) determining the change in concentration for at least one of the following 2-hydroxybutane-1,2,4-tricarboxylate, 2-oxoglutarate, acetyl-CoA, CoA, and/or $H_2O$;

wherein a change in concentration for any of the above substances between steps (a) and (b) indicates that said test compound is a candidate for an antibiotic.

5. The method of claim 4, wherein said homocitrate synthase is a fungal homocitrate synthase.

6. The method of claim 4, wherein said homocitrate synthase is a Magnaporthe homocitrate synthase.

7. The method of claim 4, wherein said homocitrate synthase is SEQ ID NO: 3.

8. A method for determining whether a compound identified as an antibiotic candidate by the method of claim 8 has antifungal activity, further comprising:

contacting a fungus or fugal cells with said antibiotic candidate and detecting a decrease in growth, viability, or pathogenicity of said fungus or fungal cells.

9. A method for identifying a test compound as a candidate for an antibiotic, comprising:

a) contacting 2-hydroxybutane-1,2,4-tricarboxylate and CoA with a homocitrate synthase;

b) contacting 2-hydroxybutane-1,2,4-tricarboxylate and CoA with a homocitrate synthase and said test compound; and c) determining the change in concentration for at least one of the following: 2-hydroxybutane-1,2,4-tricarboxylate, 2-oxoglutarate, acetyl-CoA, CoA, and/or $H_2O$;

wherein a change in concentration for any of the above substances between steps (a) and (b) indicates that said test compound is a candidate for an antibiotic.

10. The method of claim 9, wherein said homocitrate synthase is a fungal homocitrate synthase.

11. The method of claim 9, wherein said homocitrate synthase is a Magnaporthe homocitrate synthase.

12. The method of claim 9, wherein said homocitrate synthase is SEQ ID NO: 3.

13. A method for determining whether a compound identified as an antibiotic candidate by the method of claim 9 has antifungal activity, further comprising:

contacting a fungus or fungal cells with said antibiotic candidate and detecting a decrease in growth, viability, or pathogenicity of said fungus or fungal cells.

14. A method for identifying a test compound as a candidate for an antibiotic, comprising:

a) contacting acetyl-CoA and $H_2O$ and 2-oxoglutarate with a polypeptide selected from the group consisting of: a polypeptide having at least 50% sequence identity with a homocitrate synthase, a polypeptide having at least 50% sequence identity with a homocitrate synthase and having at least 10% of the activity thereof, and a polypeptide comprising at least 100 consecutive amino acids of a homocitrate synthase b) contacting acetyl-CoA and $H_2O$ and 2-oxoglutarate with said polypeptide and said test compound; and c) determining the change in concentration for at least one of the following: 2-hydroxybutane-1,2,4-tricarboxylate, 2-oxoglutarate, acetyl-CoA, CoA, and/or $H_2O$;

wherein a change in concentration for any of the above substances between steps (a) and (b) indicates that said test compound is a candidate for an antibiotic.

15. A method for identifying a test compound as a candidate for an antibiotic, comprising:

a) contacting 2-hydroxybutane-1,2,4tricarboxylate and CoA with a polypeptide selected from the group consisting of: a polypeptide having at least 50% sequence identity with a homocitrate synthase, a polypeptide having at least 50% sequence identity with a homocitrate synthase and at least 10% of the activity thereof, and a polypeptide comprising at least 100 consecutive amino acids of a homocitrate synthase b) contacting 2-hydroxybutane-1,2,4-tricarboxylate and CoA, with said polypeptide and said test compound; and c) determining the change in concentration for at least one of the following: 2-hydroxybutane-1,2,4-tricarboxylate, 2-oxoglutarate, acetyl-CoA, CoA, and/or $H_2O$;

wherein a change in concentration for any of the above substances between steps (a) and (b) indicates that said test compound is a candidate for an antibiotic.

16. A method for identifying a test compound as a candidate for an antibiotic, comprising:

a) measuring the expression of a homocitrate synthase in a cell, cells, tissue, or an organism in the absence of said compound;

b) contacting said cell cells, tissue, or organism with said test compound and measuring the expression of said homocitrate synthase in said fungus or fungal cell;

c) comparing the expression of homocitrate synthase in steps (a) and (b);

wherein a lower expression in the presence of said test compound indicates that said compound is a candidate for an antibiotic.

17. The method of claim 16 wherein said a cell, cells, tissue, or organism is, or is derived from a fungus.

18. The method of claim 16 wherein said cell, cells, tissue, or organism is, or is derived from a Magnaporthe fungus or fungal cell.

19. The method of claim 16, wherein said homocitrate synthase is SEQ ID NO: 3.

20. The method of claim 16, wherein the expression of homocitrate synthase is measured by detecting HCS1 mRNA.

21. The method of claim 16, wherein the expression of homocitrate synthase is measured by detecting homocitrate synthase polypeptide.

22. A method for identifying a test compound as a candidate for an antibiotic, comprising:

a) providing cells having one form of a homocitrate synthase gene, and providing comparison cells having a different form of a homocitrate synthase gene, b) contacting said cells and said comparison cells with a test compound and determining the growth of said cells and comparison cells in the presence of the test compound;

wherein a difference in growth between said cells and said comparison cells in the presence of said compound indicates that said compound is a candidate for an antibiotic.

23. The method of claim 22 wherein the cells are fungal cells.

24. The method of claim 22 wherein the cells are Magnaporthe cells.

25. The method of claim 22 wherein said form and said comparison form of the homocitrate synthase are fungal homocitrate synthases.

26. The method of claim 22, wherein at least one form is a Magnaporthe homocitrate synthase.

27. The method of claim 22 wherein said form and said comparison form of the homocitrate synthase are non-fungal homocitrate synthases.

28. The method of claim 22 wherein one form of the homocitrate synthase is a fungal homocitrate synthase, and the other form is a non-fungal homocitrate synthase.

29. A method for identifying a test compound as a candidate for an antibiotic, comprising:

a) providing cells having one form of a gene in the lysine biochemical and/or genetic pathway and providing comparison cells having a different form of said gene, b) contacting said cells and comparison cells with a said test compound, c) determining the growth of said cells and comparison cells in the presence of said test compound;

wherein a difference in growth between said cells and said comparison cells in the presence of said compound indicates that said compound is a candidate for an antibiotic.

30. The method of claim 29 wherein the cells are fugal cells.

31. The method of claim 29 wherein the cells are Magnaporthe cells.

32. The method of claim 29 wherein said form and said comparison form of the lysine biosynthesis gene are fugal lysine biosynthesis genes.

33. The method of claim 29, wherein at least one form is a Magnaporthe lysine biosynthesis gene.

34. The method of claim 29 wherein said form and said comparison form of the lysine biosynthesis genes are non-fungal lysine biosynthesis genes.

35. The method of claim 29 wherein one form of the lysine biosynthesis gene is a fungal lysine biosynthesis gene, and the other form is a non-fungal lysine biosynthesis gene.

36. A method for determining whether a test compound identified as an antibiotic candidate by the method of claim 29 has antifungal activity, further comprising:

contacting a fungus or fungal cells with said antibiotic candidate and detecting a decrease in growth, viability, or pathogenicity of said fungus or fungal cells.

37. A method for identifying a test compound as a candidate for an antibiotic, comprising:

(a) providing paired growth media; comprising a first medium and a second medium, wherein said second medium contains a higher level of lysine than said first medium;

(b) contacting an organism with said test compound;

(c) inoculating said first and second media with said organism; and (d) determining the growth of said organism;

wherein a difference in growth of the organism between said first and second media indicates that said test compound is a candidate for an antibiotic.

38. The method of claim 37, wherein said organism is a fungus.

39. The method of claim 37, wherein said organism is Magnaporthe.

40. An isolated polynucleotide comprising a nucleotide sequence that encodes a polypeptide of SEQ ID NO: 3.

41. The polynucleotide of claim 40 comprising the nucleotide sequence of SEQ ID NO: 1.

42. An expression cassette comprising the polynucleotide of claim 41.

43. The isolated polynucleotide of claim 40 comprising a nucleotide sequence of at least 50 to at least 95% sequence identity to SEQ ID NO: 1.

44. A polypeptide consisting essentially of the amino acid sequence of SEQ ID NO: 3.

45. A polypeptide comprising the amino acid sequence of SEQ ID NO: 3.

* * * * *